US012762357B2

(12) United States Patent
Ahrens et al.

(10) Patent No.: US 12,762,357 B2
(45) Date of Patent: Oct. 13, 2026

(54) ARTIFICIAL INTELLIGENCE COMMUNICATION ENHANCEMENTS

(71) Applicant: IQVIA Inc., Parsippany, NJ (US)

(72) Inventors: Barry Matthew Ahrens, Fayetteville, NC (US); Naouel Baili Benabdallah, Cary, NC (US); Gary Shorter, Cary, NC (US); Brian Slocum Vannah, Denver, CO (US)

(73) Assignee: IQVIA Inc., Parsippany, NJ (US)

( * ) Notice: Subject to any disclaimer, the term of this patent is extended or adjusted under 35 U.S.C. 154(b) by 43 days.

(21) Appl. No.: 18/947,868

(22) Filed: Nov. 14, 2024

(65) Prior Publication Data

US 2026/0134232 A1 May 14, 2026

(51) Int. Cl.
*G06F 40/58* (2020.01)
*G16H 10/20* (2018.01)

(52) U.S. Cl.
CPC ............. *G06F 40/58* (2020.01); *G16H 10/20* (2018.01)

(58) Field of Classification Search
USPC ..................................................... 704/1–504
See application file for complete search history.

(56) References Cited

U.S. PATENT DOCUMENTS 11,532,301 B1 12/2022 Hajebi et al.
2023/0043543 A1* 2/2023 Gnanasambandam ..................... G16H 50/70
2023/0316305 A1* 10/2023 Cella .................. G06F 21/6245
2023/0368070 A1* 11/2023 Bhargava ............... G16H 50/20
2024/0355437 A1* 10/2024 Rockne .................. G06F 40/20
2024/0362363 A1* 10/2024 Jannink ............... G06F 21/6254
(Continued)

FOREIGN PATENT DOCUMENTS

WO WO-2023097026 A2 * 6/2023 ......... G06Q 30/0202

OTHER PUBLICATIONS

Dominic et al., Knowledge Graph-Enhanced Semantic Cache for Low-Latency and Cost-Effective Inference in Large Language Models, 2024 International Conference on Information Management and Technology. Aug. 28, 2024.
(Continued)

*Primary Examiner* — Marcus T Riley
(74) *Attorney, Agent, or Firm* — ALG Intellectual Property, LLC

(57) ABSTRACT

Methods, systems, and apparatus, including computer programs encoded on computer storage media, for enhancing communications between a client device and AI/ML models. In some implementations, a method includes a system that receives multiple requests for machine learning models. The system determines whether a first request corresponds to other requests. In response to determining the first request corresponds to one or more of the other requests, the system provides, to a first user device that submitted the first request, a natural language response previously produced by the machine learning models associated with the first request. In response to determining that a second request does not correspond to any of the other requests, the system provides, to the machine learning models, the second request. The system provides, to a second user device that submitted the second request, output from the machine learning models that processed the second request.

20 Claims, 5 Drawing Sheets

(56) References Cited

U.S. PATENT DOCUMENTS

| | | | | |
|---|---|---|---|---|
| 2024/0419702 | A1* | 12/2024 | Adaboina | G16H 40/20 |
| 2025/0252485 | A1* | 8/2025 | Liila | G06Q 40/02 |
| 2025/0299255 | A1* | 9/2025 | Cella | G06Q 40/04 |
| 2025/0384341 | A1* | 12/2025 | Cella | G06N 20/00 |
| 2026/0073226 | A1* | 3/2026 | Etemadi | G06N 3/088 |
| 2026/0134005 | A1* | 5/2026 | Ahrens | G06F 16/3329 |
| 2026/0134232 | A1* | 5/2026 | Ahrens | G06F 40/58 |

OTHER PUBLICATIONS

Fu Bang et al., GPTCache: An Open-Source Semantic Cache for LLM Applications Enabling Faster Answers and Cost Savings, Proceedings of the 3rd Workshop For natural Language Processing Open Source Software. Dec. 6, 2023.

International Search Report received in PCT Application No. PCT/US2025/055265 on Mar. 18, 2026.

Li et al., SCALM: Towards Semantic Coaching for Automated Chat Services with Large Language Models, 2024 IEEE/ACM 32nd International Symposium on Quality of Service. Jun. 19, 2024.

Rasool et al., LLMs for Test Input Generation for Semantic Applications, Proceedings of the 2024 IEEE/ACM 12th International Conference on Formal Methods in Software Engineering. Apr. 14, 2024.

* cited by examiner

ARTIFICIAL INTELLIGENCE COMMUNICATION ENHANCEMENTS

TECHNICAL FIELD

This specification relates to techniques for determining and improving communications between user devices and models for artificial intelligence and machine learning.

BACKGROUND

Artificial intelligence (AI) and machine learning (ML) techniques have improved significantly and continue to gain new capabilities. For example, neural network models, such as many large language models, have shown the capability to process, generate, and output many types of natural language text. For example, computer systems that leverage large language models can respond to user prompts in text-based messaging sessions or over many conversations with various users.

SUMMARY

In some implementations, a computer system can monitor clinical trial conversations in an artificial intelligent (AI) context. The computer system can capture the interactions between a subject matter expert (SME) that communicates with one or more large language models (LLMs). The interactions can include queries sent to the LLMs, responses provided by the LLMs, and metadata associated with the queries and responses. The computer system can learn from these interactions to produce predictive and prescriptive analytics with regards to clinical trial insights and knowledge. In further detail, by capturing the interactions between the SME and the one or more LLMs, the computer system builds a knowledge database that integrates domain-specific knowledge with sophisticated clinical trial-based cache lookup. As will be further described below, the computer system leverages the knowledge database to offer predictive insights and prescriptive recommendations to aid in decision-making processes.

In some implementations, a computer system can enhance communications between a client device and AI/ML models. The computer system can generate supplemental content that is coordinated with or corresponding to a communication provided by a client device using AI/ML models and non-AI/ML models. The supplemental content can be provided to the AI/ML models along with the communication provided by the client device, e.g., a natural language query. The supplemental content can include, for example, additional metadata, corrections to the query, additional narratives associated with the query, and/or instructions for the AI/ML models to enhance processing of the query, e.g., creating visualizations, producing software instructions associated with the results, and other instructions. The AI/ML models can use the supplemental content to augment their output. In some cases, the computer system can provide the supplemental content to the AI/ML models to ensure an accurate response is produced, prevent the AI/ML models from hallucinating or timing out, and to generate predictions of subsequent queries a user of a corresponding client device is likely to request.

In some implementations, the computer system can monitor communications between the client devices and the AI/ML models. To perform the monitoring, the computer system may be positioned between the client devices and the AI/ML models over a communication network. This positioning enables the computer system to analyze, track, and accumulate the communications between the client devices and the AI/ML models. The communications can include, for example, the natural language queries submitted by each of the client devices to the AI/ML models, the corresponding natural language responses generated by the AI/ML models from processing the corresponding queries, and metadata associated with the queries and responses.

In some implementations, the computer system can build an intelligent database using the monitored communications between the client devices and the AI/ML models. For example, the computer system can acquire queries transmitted by the client devices and the corresponding natural language responses produced by the AI/ML models from processing the queries. The computer system can store these queries and corresponding natural language responses in a database. The computer system can build a large dataset by gradually storing more queries and responses over a period of time. As will be further described below, the large dataset can then be utilized to improve subsequent communications between the client devices and the AI/ML models.

For example, the computer system can capture the responses produced by the AI/ML models, which presents valuable knowledge and insights about how the AI/ML models process queries and produce responses. The computer system can capture this valuable knowledge and insights and store this information as metadata in the database. The computer system can then apply this metadata to improve the communications of subsequent query requests provided to the AI/ML models.

In some implementations, the computer system can apply the insights gleaned from the large dataset to any subsequently received query for the AI/ML models and enhance the interaction process. For example, the computer system can determine whether a subsequent received query matches to a stored query in the large dataset. If the computer system determines the subsequent query is similar to a stored query within a threshold according to a meaning of query, similar query types, or criteria, the computer system can provide the previously produced natural language response for that similar query to the user or client device that submitted the received query. In this example, the computer system does not require querying the AI/ML models with the subsequent received query because the computer system determines the previously produced natural language response for the matched query is sufficient to respond to the client device.

In another example, the computer system may determine a subsequently received query does not match to any stored query in the large dataset. However, the computer system may determine this received query is likely to cause the AI/ML models to hallucinate. The computer system can analyze the received subsequent query and determine that this query is similar to a stored query that previously caused the AI/ML models to hallucinate. Accordingly, before the received subsequent query is forwarded to the AI/ML models for processing, the computer system can modify the received subsequent query, e.g., clarify the language of the query, add more details to the query, or remove ambiguous words, to name some examples, and forward the modified query to the AI/ML models. When the AI/ML models produce the natural language response, the computer system can store the natural language response with the modified query in the large dataset and forward the natural language response and the modified query to the corresponding client device. In this manner, the computer system can automatically improve the querying of the AI/ML models, track the improvements, and recommend the improvements to the corresponding client device for future query transactions.

In some implementations, a user of the client device can perform an action or provide an input that requests or triggers the process of querying the AI/ML models. For example, a user may submit a query or natural language question on an interface of the client device. The client device can transmit the query or the natural language question to the computer system, which triggers the process of either generating enhancement or supplemental content to provide to the AI/ML models, providing the natural language question directly to the AI/ML models, or returning a previously created natural language response, to name some examples.

In some cases, the computer system can generate new and useful information to provide to the client device in response to receiving the natural language question. The computer system can analyze the characteristics of the received natural language question and leveraging the large dataset, identify other similar requests in the large dataset that have been previously processed by the AI/ML models. Supplemental content can be generated to improve the AI/ML models' processing of the query, improve the clarity of the request, and add recommended data to the request the computer system believes the user may subsequently ask, to name some examples. The computer system can forward the natural language question and the generated supplemental content to the AI/ML models for processing. In response, the computer system can provide the natural language responses output by the AI/ML models and other data to the client device that transmitted the request.

In some cases, the computer system can provide previous responses associated with the other similar requests to the client device as predictions of future queries the user may submit, predictions of responses to future queries the user may seek, visualizations of data indicative of the predicted future queries or future responses, or other data types. In this manner, the computer system can provide personalized recommendations to the client device to aid the user in gathering information. Not only does this benefit the user, but the prediction of subsequent queries and responses reduces the amount of time required for the client device to receive answers to their questions. In some cases, the computer system can trigger the prediction and/or generation of additional responses or queries according to other criteria, e.g., type information shown on the display, previous queries submitted by an authenticated user, and other information, to name a few examples.

In some implementations, the computer system can support various applications where processing tasks for responding to a user query is split between non-AI/ML or non-probabilistic data processing systems and AI/ML models. For example, when a user query, such as a natural language query is received, the computer system can leverage its large database to generate a set of supplemental data that is relevant to the natural language query. The computer system can then provide the set of supplemental data to the AI/ML models, such as one or more large language models (LLMs), to generate output in response to the natural language query. In this manner, the computer system can combine the utilizations of the AI/ML models, the non-AI/ML models, and the large dataset to provide to a client device or another internal or external application with responses that are more complete and accurate, and in a timely manner, than either type of processing capable on its own.

Generally, many AI/ML models have a strong capability to generate responses and excellent capabilities to produce high-quality natural language outputs. However, the AI/ML models may provide content that include hallucinations or may approximate responses, such as by producing responses that are generalized, guessed, or created from previous questions provided by other users and lack specificity to the current query. The AI/ML models' output may lack the technical accuracy and specificity a user seeks. As a result, the output of AI/ML models may reveal inaccuracies and incorrect answers, which can decrease users' confidence and ability to rely on correct responses.

As described below, the computer system can leverage both outputs produced by the AI/ML models and non-AI/ML models. The non-AI/ML models can utilize non-AI/ML models such as mathematical models, database systems, and other determinations, which are repeatable and non-probabilistic. In this manner, the non-AI/ML models can focus on a particular dataset of interest to aid the processing of the AI/ML models or focus on the particular dataset of interest while the AI/ML models focus on a separate feature of processing. In this manner, the combination of the processing performed by the non-AI/ML models and processing performed by the AI/ML models enable the two models to work in tandem in responding to the user query. The output can include the reliability and predictable nature of the non-AI/ML models along with text and natural language responses produced by the AI/ML models.

Combining the functionality of the different models can provide users with higher confidence of using the computer system. In many cases, the AI/ML models may process only the metadata of a data set, which describes the general contents and/or structure of the data set, e.g., data types, metrics, and other attributes, and information directed to how the AI/ML model is to produce output, e.g., stylistic information, formatting, and other data types. This enhances the speed and reduces network transfer requirements because the entirety of the dataset itself does not need to be sent over the network to the AI/ML models and the dataset does not need to be processed by the AI/ML models.

In some implementations, by relying on multiple processing systems, e.g., the computer system with the non-AI/ML models and a separate system with the AI/ML models, the architecture of this system offers increased flexibility in specifying the types of components used in generating the responses. This architecture provides for flexible customization in allowing not only administrators but users, which of the different AI/ML models or different non-AI/ML models they desire to be used for processing. Moreover, the computer system includes the flexibility to determine whether the separate system with the AI/ML models are used, or whether a previous response produced by the AI/ML models can be provided in response to a query. In this manner, this level of customization provides flexibility in determining which components produce its output and components selected by the administrators optimized for executing.

In one general aspect, a method performed by one or more computers includes: receiving multiple requests related to clinical trial data for querying one or more machine learning models; determining whether a first request of the multiple requests corresponds to one or more other requests that previously queried the one or more machine learning models; in response to determining that the first request of the multiple requests corresponds to one or more of the other requests: retrieving a first natural language response previously produced by the one or more machine learning models associated with the first request; and providing, to a first user device that submitted the first request, the first retrieved natural language response; determining whether a second request of the multiple requests corresponds to one or more other requests that previously queried the one or more machine learning models; and in response to determining that the second request does not correspond to any of the one or more other requests: providing, to the one or more machine learning models, the second request; and providing, to a second user device that submitted the second request, a second natural language response to the second request output from the one or more machine learning models.

Other embodiments of this and other aspects of the disclosure include corresponding systems, apparatus, and computer programs, configured to perform the actions of the methods, encoded on computer storage devices. A system of one or more computers can be so configured by virtue of software, firmware, hardware, or a combination of them installed on the system that in operation cause the system to perform the actions. One or more computer programs can be so configured by virtue having instructions that, when executed by data processing apparatus, cause the apparatus to perform the actions.

The foregoing and other embodiments can each optionally include one or more of the following features, alone or in combination. For example, one embodiment includes all the following features in combination.

In some implementations, the method includes receiving the multiple requests related to the clinical trial data for querying the one or more machine learning models includes receiving the multiple requests provided by a respective user through an interface of a respective user device, each request of the multiple requests including a natural language question for querying the one or more machine learning models.

In some implementations, determining whether a given request of the multiple requests corresponds to one or more other requests that previously queried the one or more machine learning models includes: identifying characteristics of the given request, wherein identifying the characteristics of the given request includes: parsing words in the given request into separate words; identifying a number of parsed words in the given request; identifying a meaning of each parsed word in the given request; and identifying a contextual domain of the given request using the meaning of each parsed word and the number of parsed words in the given request.

In some implementations, determining whether a given request of the multiple requests corresponds to one or more other requests that previously queried the one or more machine learning models includes: for each other request of the plurality of other requests: comparing the contextual domain of the given request with a contextual domain of the other request; determining whether the comparison between the contextual domain of the given request and the contextual domain of the other request correspond to one another according to a threshold metric; and in response to determining the comparison satisfies the threshold metric, retrieving the other request and a natural language response that was produced by the one or more machine learning models from processing the other request.

In some implementations, the method includes: in response to determining that a given request of the multiple requests corresponds to the one or more of the other requests: modifying, using data from one or more other requests identified as corresponding to the given request, the given request for querying the one or more machine learning models, the modifying comprises: modifying, using the data from the one or more other requests identified as corresponding to the given request, the given request by adjusting at least one of (i) a semantics of the given request, (ii) a number of words of the given request, (iii) data types of words in the given request, (iv) word types in the given request, and (v) order of the words in the given request; providing, to the one or more machine learning models, the modified given request; and providing, to the user device, another output from the one or more machine learning models that processed the given request.

In some implementations, the method includes: in response to determining that a given request corresponds to the one or more other requests: comparing criteria of the given request to criteria of a set of the one or more other requests, the set of other requests having previously caused the one or more machine learning models to hallucinate, break, or time out; based on the comparison, determining whether the criteria of the given request satisfy the criteria of the set of the one or more other requests; in response to determining that the criteria of the given request satisfy at least one criterion of the set of the one or more other requests, predicting that the given request is likely to cause the one or more machine learning models hallucinate, break, or time out; and in response to the prediction, modifying, using data from a second set of other requests, the given request to prevent the one or more machine learning models from hallucinating, breaking, or timing out in response to processing the given request.

In some implementations, the method includes: providing, to the one or more machine learning models, the modified given request; obtaining another output from the one or more machine learning models that processed the given request; identifying that the another output indicates the one or more machine learning models did not hallucinate, break, or time out in response to processing the given request; and providing, to a user device the other output from the one or more machine learning models and data indicating the modification to the given request.

In some implementations, providing the second request comprises transmitting, over a network and to the one or more machine learning models, the second request and metadata associated with the second request selected from a database.

In some implementations, the method includes providing, to the one or more machine learning models, a request for one or more software instructions utilized by the one or more machine learning models in producing the second natural language output for processing the second request.

In some implementations, the method includes: obtaining the second natural language output from the one or more machine learning models that processed the second request; storing, in a database, the obtained output and one or more software instructions from the one or more machine learning models with the second request; generating output from locally executing, using one or more processors, one or more software instructions using data from the database, the one or more software instructions utilized by the one or more machine learning models in producing the output for processing the second request; and comparing the (i) generated output from locally executing the one or more software instructions received from the one or more machine learning models and (ii) the obtained output from the one or more machine learning models.

In some implementations, in response to comparing the (i) generated output from locally executing the one or more software instructions received from the machine learning models and (ii) the obtained output from the one or more machine learning models, the method includes providing, to the second user device, data indicative of the obtained output that processed the second request in response to determining the generated output corresponds to the obtained output.

In some implementations, in response to comparing the (i) generated output from locally executing the one or more software instructions received from the machine learning models and (ii) the obtained output from the one or more machine learning models, the method comprises: determining whether the generated output does not correspond to the obtained output from the one or more machine learning models; or determining whether the local execution of the one or more software instructions received from the one or more machine learning models is unable to be executed; and in response to determining that the generated output does not correspond to the obtained output or determining that the local execution of the one or more software instructions received from the one or more machine learning models is unable to be executed, providing, to the second user device, data indicating that the one or more machine learning models cannot process the second request.

In some implementations, the method includes: monitoring communications between multiple user devices and the one or more machine learning models, wherein the monitoring includes: obtaining the plurality of other requests that previously queried the one or more machine learning models; obtaining a plurality of natural language responses from the one or more machine learning models associated with the plurality of other requests; in response, generating metadata for each other request of the plurality of other requests and for each natural language response of the plurality of natural language responses; and storing, in a database, the plurality of other requests, the corresponding plurality of natural language responses, and the corresponding metadata, wherein each other request, corresponding natural language response, and corresponding metadata is stored in an indexable fashion.

In some implementations, the method includes: in response to determining that the first request corresponds to the one or more of the other requests, predicting one or more subsequent queries a user device is likely to submit based on (i) the first request and (ii) the one or more other requests that previously queried the one or more machine learning models; and transmitting, over a network, the one or more subsequent queries to the user device as recommendations, wherein the one or more subsequent queries are recommended to a user of the user device as queries the user is likely to subsequently provide.

The subject matter described in this specification can be implemented in various embodiments and may result in one or more of the following advantages. For example, the computer system that leverages the knowledge database enhances data privacy and security for the sensitive nature of the subject matter of clinical trial data. This information can be utilized in a manner that aids in the querying process of LLMs while retaining the sensitive nature of the clinical trial information. Moreover, the computer system offers a plug-and-play architecture that takes advantage of an LLM that meets security, performance, and cost. In further detail, by positioning the computer system between the SMEs and the LLMs, the broker can capture valuable and timely SME knowledge and insights directly from the interaction with the LLM and utilize those insights during future interactions.

The techniques provided in this specification describe a technical improvement to a computer system that utilizes trained machine learning models. Specifically, the techniques provide an improvement in detecting one or more received requests that may be similar to previous requests, and preventing the LLMs from being queried based on those requests. When such a similar request is received, the computer system filters that request, thus preventing an LLM query, and instead the system returns a response that was previously produced by the LLMs in association with those previous similar requests.

Here, a machine learning model may be trained using a particular training algorithm, such as gradient descent to name an example, which is an optimization algorithm to minimize differential real-valued functions in an iterative manner. The computer system can utilize the trained machine learning model to detect requests that are similar to previously received requests and filter those requests, thus preventing LLM queries based on those requests. This is important for users seeking quick and accurate results when querying the LLMs is costly and a time intensive and computationally intensive process. By automatically detecting similar queries using the trained machine learning model, the computer system enhances LLM utilization by allowing for automatic and proactive preventative measures to avoid clogging the LLM with similar and repeated queries. This system can detect that a received query matches to a query that was already processed by the LLM, and can take preventative actions, such as returning, to the client device, the already processed response of the LLM to the previously processed similar query, without the need for alerting an administrator or user. Unlike conventional systems which make use of query-response transactions with an LLM, the disclosed system can identify previously submitted queries, and take actions to return LLM-produced responses in real time without having to query the LLM. This system realizes an improvement in LLM utilization by avoiding the delay involved in an LLM transaction by automatically returning a previously produced response, which improves network efficiency, reduces computational demands, reduces the time for a user to receive a response to a query, all based on characteristics identified by the trained machine learning model at the computer system in real time.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements. The components shown here, their connections and relationships, and their functions, are meant to be examples only, and are not meant to limit the implementations described and/or claimed in this document.

DETAILED DESCRIPTION

Figure 1:
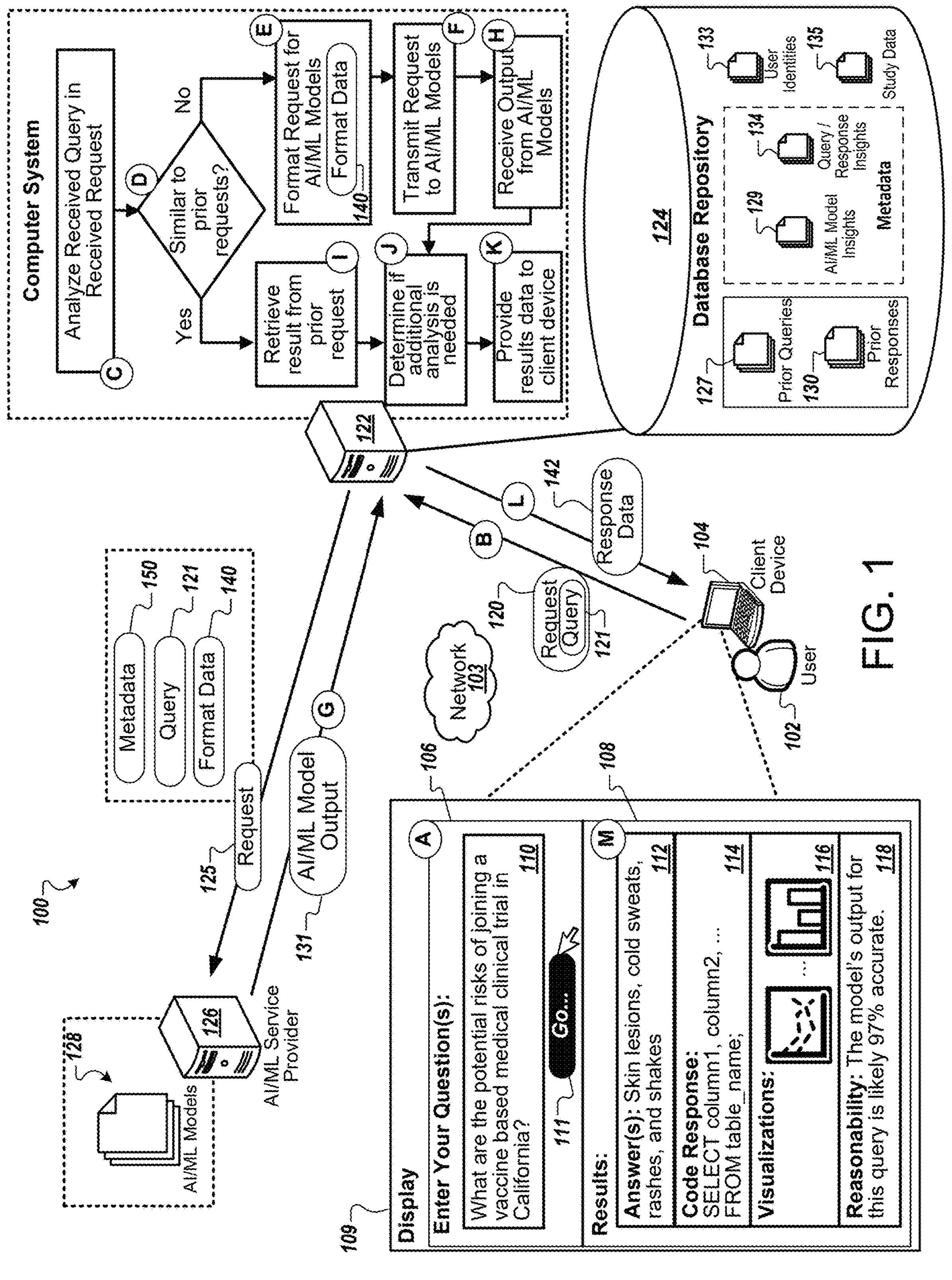
FIG. 1 is a diagram showing an example of a computer system that enhances communications between a user device and one or more artificial intelligence or machine learning (AI/ML) models.

In some implementations, a subject matter expert (SME) can pose or prompt natural language questions to large language models (LLMs) to aid in answering questions related to clinical trials or other topics. The LLMs produce a natural language response in response to processing the natural language questions. Additionally, the LLMs can produce code, software, and reasonability output that augment the natural language response. A computer system, positioned between the SME and the LLMs, can utilize the output code, software, or reasonability output to produce visualizations associated with the natural language response. This aids in the explanation to the SME and reduces burden on the SME to process and understand the natural language response.

Moreover, a computer system can be inserted in-between the SME and the LLMs to monitor and capture every interaction between the SME and the LLMs. The computer system can store these interactions, along with sufficient metadata, to create an intelligence database of clinical trial specific knowledge that provides SME and LLM knowledge and insights. Using the intelligence database, the computer system can offer predictive insights and prescriptive recommendations to aid an SME posing natural language questions relating to clinical trial information. Moreover, the computer system can continuously learn from expert interactions initiated by SMEs by monitoring the SMEs subsequent interactions with the LLMs. These knowledge and insights include domain-specific customization and offer scalability to leverage relevant clinical trial insights and knowledge.

The intelligence database offers various enhancements for the SMEs. For example, the utilization of the intelligence database offers enhanced data privacy and security for storing the sensitive nature of clinical trial data. Additionally, the utilization of the intelligence database mitigates the cost of querying expensive LLMs by relying on previously produced natural language responses in response to SMEs' natural language queries. By integrating clinical trial specific information into the intelligence database, incorporating a tandem computer system with LLMs, offering secure storage, and reducing costs, the computer system can offer domain specific content that would otherwise not be available with typical LLM interactions.

For subsequent queries, the computer system can leverage the intelligence database in responding to the subsequent queries by determining whether a received subsequent query is similar to a stored query in the intelligence database or whether to query the LLMs with the received subsequent query. In this manner, the intelligence database offers multiple uses, e.g., a reduction of time to final answer (TTFA), reduction of monetary cost in pay-per-use of the LLM, an increase in answer accuracy, and an establishment of a reusable Question-Answer interaction.

In some implementations, a computer system includes components that enhance the interactions between client devices and artificial intelligence and machine learning (AI/ML) models. The AI/ML models can be large language models (LLMs) that respond to natural language queries provided by the client device. In some cases, the computer system may be positioned between the client devices and the AI/ML models. In some cases, the computer system may incorporate and leverage localized AI/ML models. In this manner, the computer system can monitor, over a network, the interactions between the client devices and the AI/ML models. This enables the computer system to extract and store valuable information gleaned from the interactions with the AI/ML models. The interactions can include, for example, natural language queries provided by the client devices, natural language responses produced by the AI/ML models from processing the natural language queries, and metadata describing both the queries and corresponding responses.

The computer system can build an intelligent database from interactions between the client devices and the AI/ML models. Each request transmitted by the client device to the AI/ML models can be extracted and stored in the intelligent database by the computer system. When the AI/ML models produce a response from processing the request, the computer system can store that response with the corresponding request in the intelligent database. In this manner, the computer system can create an indexed database that stores the collective query and response from the interaction with the AI/ML models. Additionally, the computer system can store metadata from the monitored interactions. The metadata can include, for example, data that describes semantics of the query, identifier data of the client device that transmitted the request, a date the request was submitted, a time stamp, domain data associated with the request, instructions provided to the AI/ML models, and data types produced by the AI/ML models. The computer system stores the metadata with the monitored interactions as a way to track important insights associated with the AI/ML models to aid the processing of subsequent queries monitored by the computer system.

In some implementations, the computer system can leverage data stored in the intelligent database to improve the communications between the client devices and the AI/ML models. The improvements can include, for example, ensuring accurate information is produced by the AI/ML models, guiding the AI/ML models to produce information of interest to the user, reducing the amount of time the client devices receive a response to its query, and reducing the monetary cost of using the AI/ML models.

In some implementations, the AI/ML models may require a "pay-per-use" subscription service. If a user needs the AI/ML models to produce a large number of responses, then the costs for querying the AI/ML models can be significantly expensive. By leveraging data stored in the intelligent database to produce responses, the computer system can reuse previous responses produced by the AI/ML models without having to re-query the AI/ML models. Not only can the system produce supplemental information to improve the responses produced by the AI/ML models, but the system can preclude the querying of the AI/ML models by returning a natural language response already produced by the AI/ML models from a query that matches to a previously stored query or matches to the previously stored query or queries that satisfies a threshold.

In some implementations, the computer system can provide accurate and customized content for a user to supplement a particular request. The computer system can receive a query from a client device and determine one or more enhancements that the user is likely to recommend. For example, the one or more enhancements can include various visualizations, e.g., charts, graphs, maps, tables, videos, or other, that are dynamic for processing a particular data set and include additional enhancements to those various visualizations, e.g., filtering, forecasting, selecting, and other calculations. The computer system can utilize the non-AI/ML models to produce various graphs using data stored in its database. The computer system can access the data stored in the database used to create the database and request a selected one of the AI/ML models to process the data, e.g., to summarize relevant information shown in the visualization, to annotate certain attributes or metrics shown in the visualization, or to describe predictions according to the various data shown in the visualizations.

In some implementations, the computer system can instruct the AI/ML models to produce data in addition to the natural language response. In an example, the computer system can instruct the AI/ML models to produce software instructions used to produce the output from the natural language query. In another example, the computer system may rely on the non-AI/ML models to produce data in a predictable manner, such as performing determinable calculations, relational database functions, and other functions. The AI/ML models may be provided with software instructions to describe how the non-AI/ML models produced the predictable data from calculations, for example. More specifically, in this example, the computer system specifies the type of software code for the produced software instructions, e.g., a structured query language (SQL) statements, Python code, JAVA code, or other, to name some examples.

The computer system can be configured to automatically perform additional functions to improve the querying of the request to the AI/ML models. These automatic functions can be performed in addition to the scope of the functions sought after in original query. For example, the computer system can be configured to analyze different data sets at different time periods, identify trends in various data sets, forecasting, perform regression modeling, and aggregate data sets together. In some cases, the computer system can include various machine learning (ML) models or other techniques not available to the LLMs. In this manner, the computer system offers various functionality to users seeking responses to requests that extends beyond the capability of the LLMs and extends beyond the functionality requested for by the user. As a result, the computer system can offer a more detailed analysis, more accurate data, offer different answer types, calculate relationships, trends, and provide forecasts. However, the results of these non-AI/ML models and the ML models produced can be provided to the AI/ML models for processing by the one or more LLMs. The one or more LLMs can produce detailed narratives of the analysis data, highlight or tag important information relevant to the user, structure the information in a desired manner, and produce one or more natural language responses for the client device.

In one such example, the user may provide a query for analyzing data trends of vaccine effectiveness across at different medical trials around the country. The computer system can receive the query and determine that the query is similar to one or more other queries that requested for data trends. In those other queries, the computer system provided visualizations to the user to improve the understanding of data trends. The computer system can retrieve data from its database that stores various data types associated with the different medical trials, e.g., vaccine effectiveness data across various patients. Various non-AI/ML models and machine learning models located at the computer system can process the retrieved data to produce different analysis of data trends, e.g., data showing ineffectiveness or effectiveness over a period of time, predictions of similar vaccine effectiveness at other locations, predictions of different vaccine effectiveness at similar clinical trial locations, and factors that contributed to the predictions. The computer system can generate a request that includes the data types of the provided visualizations, metadata describing the produced visualizations, and a summary of analysis of different data trends, e.g., trend analysis, regression analysis, and forecasting analysis. The computer system can transmit the generated request to the AI/ML models, which produces one or more natural language responses that describe the analyzed data trends of vaccine effectiveness across the different medical trials. The computer system can then present the analysis data provided in visualization format and the one or more natural language responses to the client device of the user that submitted the query for their review.

In some implementations, the process of producing additional information and querying the AI/ML models to prevent it from producing false data can be transparent to the end user. The end user provides a single query to the computer system, and the computer system can analyze the single query to perform one or more additional functions without requiring the user to provide any additional instructions. This ensures that the computer system automatically gathers appropriate data and performs functions that the computer system believes the user is likely to find important or has previously found important. In this manner, the system increases the speed at which a response is provided to the user because the computer system does not wait for the user to approve, deny, or formulate additional queries or instructions that need to be transmitted across the network. Instead, the computer system may even provide additional supplemental information to the user device even if the user did not ask for such information because the system predicts the user is likely to ask for such information in the future.

FIG. 1 is a diagram showing an example of a computer system that enhances communications between a user device and one or more artificial intelligence or machine learning (AI/ML) models. FIG. 1 illustrates various operations in stages (A) though (M), which may be performed in the sequence indicated, in another sequence, with fewer operations, or additional operations.

In some implementations, the system 100 includes a computer system 122, a database repository 124, and an AI/ML service provider 126. The system 100 also includes a client device 104 and a user 102. The various components of system 100 communication over a network 103, such as the Internet or other. The computer system 122 coordinates various operations between the client device 104 and the AI/ML service provider 126 to provide and manage access to previous requests, previous responses, AI/ML applications, and non-AI/ML applications. The computer system 122 can store in the database repository 124 data associated with previous requests, previous responses produced by the AI/ML models, metadata, and data identifying client devices that communicate with the computer system 122. The computer system 122 can also store data associated with prior inputs and outputs of various models, prior versions of the AI/ML models, and supplemental data produced by the computer system 122.

In the example of FIG. 1, the user 102 has loaded an interface on a display 109 of the client device 104. The display 109 illustrates the interface with various components, e.g., a user interface element 106 for entering a natural language query and a user interface element 108 for receiving a natural language response to the provided natural language query. The user interface element 106 includes a text box 110 that enables the user to provide the natural language query either by typing, speaking, or interacting with the interface on the client device. In response to submitting the natural language query or question in the text box 110, the user 102 can select the "Go" button 111 to transmit the request to the computer system 122. The computer system 122 can process with the request with the aid of the AI/ML models and other components, and return a natural language response and other information in the user interface element 108.

The user interface element 108 includes various separate interface elements for providing a response to the natural language query. For example, the user interface element 108 includes an answer user interface element 112, a coding user interface element 114, a visualization user interface element 116, and a reasonability user interface element 118. The answer user interface element 112 includes a text box that provides a natural language response to the natural language query provided in the text box 110. The natural language response provided on the display 109 includes the output text produced by the computer system 122. The coding user interface element 114 includes a text box that provides software or code illustrating how the AI/ML models arrived at the response shown in the user interface element 112. The visualization user interface element 116 includes one or more visualizations, e.g., graphs, charts, tables, videos, maps or other, that aid in understanding the natural language response provided in the answer user interface element 116. In some cases, the reasonability user interface element 118 includes a description that describes the accuracy of the AI/ML models' output. This description provides the user with the confidence or lack of confidence in the AI/ML models' answer in processing the natural language query.

In some cases, the display 109 may illustrate other user interface elements. These other user interface elements can include, for example, selectable options for the user 102. For example, the user 102 can select on the interface of the display 109 whether the data for each of the above-mentioned interface elements should be processed in response to submitting the natural language query to the computer system 122. The display 109 may also include other user interface elements, such as, for example, the option to select a particular AI/ML model for processing the natural language query, the option to view the reasoning and thoughts of the AI/ML model for producing the natural language response, and an option for the computer system 122 to select the closest natural language response to provide to the natural language query.

In some implementations, the option to select a particular AI/ML model provides the user 102 with flexibility. The client device 104 can present one or more AI/ML models offered by the AI/ML service provider 126, and the user 102 can select which of the one or more AI/ML models to be used for processing the natural language query. In some cases, each AI/ML model can be trained for a relevant data type, and the user 102 may select which AI/ML model processes the natural language query. Generally, the AI/ML service provider 126 can determine which of the AI/ML models processes the natural language query if the user 102 does not select this option.

In some implementations, the option to view the reasoning and thoughts of the AI/ML model for producing the natural language response allows the user 102 to view how the AI/ML model arrived at its answer. The reasoning and thoughts may be provided in the form of software code, debugging output, a graphical representation, one or more processes taken by the AI/ML models to produce the natural language response, and one or more processes taken by the computer system 122 to produce the natural language response. For example, the computer system 122 may use various ML models and non-AI/ML models for producing the answers, the code response, the visualizations, and the reasonability answer. As a result, the reasoning and thoughts may describe processes taken not only by the computer system 122 but also the AI/ML models in producing the answers.

In some implementations, the option for the computer system 122 to select a closest natural language response to provide to the natural language query allows the user 102 to preclude the use of the AI/ML models. In this case, the user 102 may desire not to use the AI/ML models and instead instruct the computer system 122 to produce a previously created natural language response to the natural language query provided in the text box 110. The user 102 may not want to pay to utilize the AI/ML models, or the user 102 may want to evaluate the accuracy of the large database created by the computer system 122. Either way, the computer system 122 will not forward the natural language query to the AI/ML models in this example, and will locally process the natural language query and provide a natural language response that was previously produced by the AI/ML models from a previous query and also likely answers the natural language query.

The process for obtaining the information shown on the display 109 can be quite simple and seamless to the user 102. The interface of the display 109 enables a user 102 to trigger the processing of a natural language query and presentation of various enhancements. When the user 102 interacts with the interface on the display and submits the natural language query in the text box 110 by interacting with the go button or user interface element 111, the computer system 122 can generate a natural language response using the natural language query and data stored in the large database. As a result of a single user interface, and with no need to ask the user to provide additional questions, the computer system 122 can generate and provide additional information, e.g., such as the information indicated in user interface elements 112 to 118, even if the user 104 has not selected for such options to be shown. The computer system 122 can make predictions as to which data will be beneficial for the user 102 to view on the display 109.

The example of FIG. 1 includes stages (A) to (N), which represent various operations and a flow of data, which can occur in the order illustrated, in a different order, and more or fewer operations.

The computer system 122 can be implemented using one or more servers, such as one or more cloud computing systems, one or more on-premises servers, etc. In some examples, the computer system 122 can be an application server or a computing server. The computer system 122 can provide front-end functionality to interface with one or more client devices in real or substantially real time. For example, the computer system 122 can provide an interface to each client device for interacting with the AI/ML models offered by the AI/ML service provider 126. The interface on each client device can include an application programming interface (API), a user interface (e.g., such as by providing a web page, a web application, or a local application) or another type of user interface.

The database repository 124 can provide various data retrieval, data processing, and data storage functions. For example, the database repository 124 can be a database management system (DBMS) and can include the capability to process operations specified in structured query language (SQL), Python code, Java code, or in other forms. The database repository has access to various datasets, which can be related to previous queries by various client devices, previous natural language responses produced by the AI/ML models, metadata describing the queries and responses, user identities, and other data types. The database repository 124 can store and use datasets in any of various data types, such as tables, data files, or other data types.

For example, as illustrated in FIG. 1, the database repository can store prior queries 127 and corresponding prior responses 130. The database repository can also store metadata associated with the prior queries and the prior responses. The metadata can include AI/ML model insights 129 and query/response insights 134. The database repository can further store user identities 133. In some examples, the database repository can store other data sets such as study data 135. The study data 135 can include clinical trial data, operational data, and other study data.

As mentioned, the prior queries 127 can include queries supplied by one or more client devices to the AI/ML models. The prior queries 127 can include one or more natural language queries submitted by the one or more client devices, including the client device 104. The prior queries 127 can additionally include options selected by each user associated with the client device, such as the options to display a code response, visualizations, and reasonability, for the corresponding submitted query.

The prior responses 130 can include responses produced by the AI/ML models in response to processing the queries in the prior queries 127. The prior responses 130 can include one or more natural language responses produced by the AI/ML models in response to processing each of the one or more corresponding natural language queries submitted by the one or more client devices. The natural language responses can include, for example, descriptions produced by the AI/ML models in processing the natural language queries, inputs and output for non-AI/ML models associated with processing the corresponding natural language query at the computer system 122, and other data types processed by the non-AI/ML models and ML models at the computer system 122.

In some cases, the prior responses 130 stores feedback data associated with each prior response. The feedback data includes data designated by a user that received the prior response and notified the computer system 122 whether the prior response was it good or bad response. For example, the user 102 can submit a query to the AI/ML models 128 through the client device 104. The AI/ML models 128 processes the query and provides a response back to the client device 104. The computer system 122 monitoring this interaction stores the request and the corresponding response, and asks the user 102 through the client device 104 whether the response properly answered the query. The client device 104 can receive from the user 102 the feedback indicating whether the AI/ML models 128 properly answered the question. The client device 104 can provide the feedback to the computer system 122 and the computer system 122 can store the feedback with the requesting corresponding response.

In some cases, the computer system 122 may discard the query and corresponding response if the computer system 122 receives bad feedback from the client device 104. In some cases, the computer system 122 may store the query and corresponding response in the database repository 124 if the feedback is bad in order to detect future queries that the AI/ML models 128 struggles to process. For example, the computer system 122 can flag potentially problematic subsequent queries to the user 102 and/or modify potentially problematic subsequent queries in order for the AI/ML models 128 to produce proper outputs. If the computer system 122 receives positive feedback from the client device 104, then the computer system 122 stores the query and the corresponding response in the database repository 124.

In some implementations, the database repository 124 can store a cost associated with querying the AI/ML service right at 126. The cost may be for example if dollar amount or a credit amount. Thus, each time the client device 104 queries the AI/ML service provider 126, the AI/ML service provider 126 charges the client device 104 a cost. The AI/ML service provider 126 includes the cost in the response output to provide back to the client device 104. The computer system 122 stores the cost with the prior queries 127 and the database repository 124.

The metadata includes data that describes the prior queries 127 and the corresponding prior responses 130. In further detail, the metadata can reference each of the queries in the prior queries 127 and each of the responses in the prior responses 130. The metadata may reference each of the queries and the prior responses using, for example, indexes, pointers, address references, or any other type of data that references the responses or queries in the database repository. In this manner, and as will be further described below, when the computer system 122 receives a request from a client device, such as client device 104, the computer system 122 can analyze the metadata in the database repository to determine whether a received query matches to one or more of the stored queries in the database repository. If the computer system 122 determines that a received query matches to one or more stored queries in the prior queries 127, then the computer system 122 can retrieve a corresponding response from the prior response is 1:30 to provide back to the client device 104. This process will be further described below.

The metadata can include, for example, AI/ML model insights 129 and the query/response insights 134. The AI/ML model insights 129 includes extracted or gleaned from the processing of the AI/ML models at the AI/ML service provider 126. This can include the code response produced by the AI/ML models when generating the natural language responses, the descriptions of visualizations produced by the AI/ML models highlighting important features and/or describing aspects of the visualizations, and reasonability output by the AI/ML models. The AI/ML model insights 129 can also specify the version and type of AI/ML models that produced the prior responses, for example. The AI/ML model insights 129 can store various insights associated with the production of natural language responses produced by the AI/ML models.

In some implementations, the database repository can store query/response insights 134. The computer system 122 can receive queries, process queries, provide queries to the AI/ML models, and extract meaningful data from the queries and the responses to produce the query/responses insights 134. For example, the computer system 122 can extract semantics from the queries, language types of the queries, particular words used in the queries, and other data associated with the queries, and store that data in the query/response insights 134. The semantics of the queries can include a meaning of the query, a context or contextual domain of the query, synonyms of the words in the query, an order of the words in the query, data identifying the words in the query, and a number of words in the query. Similarly, the computer system 122 can extract semantics from the natural language responses, the language types of the natural language responses particular words used in the natural language responses, and other data associated with the natural language responses and store that data in the query/response insights 134. As will be further described below, the computer system 122 can use the data in the query/response insights 134 when seeking to identify whether a received query matches to a previously provided query. Similarly, the computer system 122 can use the data in the query/response insights 134 when seeking to identify a natural language response associated with a query that matches to a received query.

In some implementations, the database repository can store user identities 133. The authentication data can include, for example, a login session identifier indicating whether a user's client device is in session with the computer system 122, token identifiers for the user and/or the user's client device, and payment information associated with the user for utilizing the AI/ML models at the AI/ML service provider 126. In some implementations, the computer system 122 can utilize encryption of store data, anonymization, and compliance with healthcare privacy regulations to enhance security.

The user identities 133 may include profiles of users authenticated to utilize the computer system 122. In this manner, the persona of the user is captured by the computer system 122. For example, each persona is correlated to a specific set of queries and focus areas in clinical analytics. Thus, the computer system 122 can adjust predictions and recommendations based on the user persona. The session identifier signals to the computer system 122 that the client device for a particular user of that profile is authenticated and currently interacting with the system 100. When the client device 104 exits from, logs out, or ceases interacting with the computer system 122, then the computer system 122 deactivates the session identifier, signaling that the client device 104 is no longer interacting with the AI ML models.

In some implementations the data repository can store study data 135. The study data 135 can include, for example, operational and clinical structured data. One example of a structured data format is the studied data tabulation model (SDTM) format, which defines a standard structure for human clinical trial data tabulations and for non-clinical study data tabulations that can be submitted as part of an application to a regulatory authority. The SDTM data stores observations collected about subjects who participated in a clinical trial period, and each observation can be described by a series of variables, each of which corresponds to a row in a data set or table. Each variable can be classified according to a role, and each role determines the type of information conveyed by the variable about each distinct observation and how it can be used. This can be useful in a clinical trial, which describes a lab test, a start data and end date of the trial, tests performed, study day, adverse events, and severity of adverse events, to name some examples. The SDTM model is complex as a typical version can include over 100 tables or views with over 3500 attributes or fields. Moreover, a single study may have millions and millions of rows of data. In addition to the SDTM format, other data models and data types are also supported.

For example, observations for an SDTM model can be collected for subject in a series of domains. A domain or contextual domain can be defined as a collection of logically related observations with the topic specific of all subjects in a clinical trial. Each domain can be represented by a data set. The data structure for observations may include, for example, a flat file that represents a table with one or more rows or columns. Each data set may be submitted for a particular domain. Each row of the data set could represent a single observation and each column represents one of the variables. Each data set or table can be accompanied by metadata that provide information about the variables used in the data set.

The computer system 122 can use various formats to interact with the SDTM model in the study data 135. For example, the SDTM model can include study details about a therapeutic area, a trial phase, a site, and a sponsor. The study data 135 can also include details about users involved in the clinical trial data, such as their names and other personal information, location information of the clinical trial, dates of the clinical trial, timestamps associated with events in the clinical trial, and the type of medicine under study in the clinical trial. In some examples, the computer system 122 can use the data in the study data 135 to verify outputs produced by the AI/ML models at the AI/ML service provider 126. This will be further described below.

In some implementations, the database repository can store data other than study data 135. This data can include information accessed on the Internet, such as, information stored in various knowledge databases and other third-party databases. The type of data that can be accessed can include, for example, engineering data, healthcare data, payroll data, demographic information, financial information, and other data types. The computer system 122 can select which data to process when verifying the outputs produced by the AI/ML models at the AI/ML service provider 126.

In some implementations, the AI/ML service provider 126 can include or be a server system or cloud computing platform that provides access to one or more AI/ML models 128, such as LLM's. The computer system 122, the database repository 124 and the AI/ML service provider 126 may be implemented as separate systems or may be integrated in a single system. For example, the AI/ML service provider 126 can be a third-party service or can be managed and operated by the same party as the computer system 122 and or the database repository. In some examples the client devices of the system 100 can directly interact with the AI/ML service provider 126 without the computer system 122 monitoring those interactions.

In some implementations, the one or more AI/ML models 128 can be included in the computer system 122 as one or more AI/ML agents. These agents may be, for example, LLM agents, incorporated in the software of the computer system 122. In this instance, the LLM agents, which may be instantiations of the LLMs at the AI/ML models 128, may provide capabilities associated with the LLM along with adding additional layers of functionality provided by the computer system 122. The additional layers of functionality may include, for example, processing data in a database, generating software, producing visualizations, and other relevant functions, to name some examples.

In some examples, different users may have access to different data in the database repository, depending on their roles, permissions, and authentication access level, etc. As previously mentioned, the user 102 can authenticate to the computer system 122, so that the user's identity is determined, the permissions of the user 102 is determined, and so that the computer system 122 can initiate the session identifier associated with the user 102 for interacting with the system 100. In response to the user being authenticated, the user can submit requests to the computer system 122 to generate one or more natural language responses.

In the example of FIG. 1, in stage (A), the client device 104 displays an interface on display 109. The user 102 can provide a natural language query on the interface in the text box 110. The natural language query can be submitted by the client device 104 to the AI/ML models 128 of the AI/ML service provider 126. In some cases, the client device 104 can submit the natural language query to the computer system 122. In some cases, the client device 104 can submit the natural language query to the AI/ML service provider 126 and the computer system 122 can monitor the flow of communications between the client device 104 and the AI/ML service provider 126.

After the user 102 submits the natural language query in the text box 110, the user 102 can trigger the creation and or generation of a natural language response by interacting with the user interface element 111, which is shown on the user interface of the display 109. For example, the user 102 can interact with the user interface element 111 with a mouse click, a touch screen press with a finger, a vocal command to the client device 104, or another interaction that causes the client device to activate the user interface element 111. When the user 102 interacts with user interface element 111, the client device 104 generates a request 120 for the computer system 122 to provide a natural language response and other data to display on user interface of the display 109 of the client device 104. A similar process occurs for other client devices interacting with the computer system 122 and/or the AI/ML models 128.

In stage (B), the client device 104 transmits the request 120 to the computer system 122 over the network 103. The request 120 can include various types of information that describe the characterizations selected by the user 102 for producing a natural language response to the natural language query. This information in the request 120 can provide additional information that facilitates the computer system 122's natural language response generation. For example, the request 120 can include a query 121 or instruction provided by the user 102, a session identifier for a current session of an application executing on the client device 104 that displays the interface on the display 109, a user selection status, e.g., which indicates if any user interface elements have been selected or highlighted and identifiers for which of the user interface elements have been selected or highlighted, a client device identifier for the client device 104, and other data types. As illustrated in the text box 110, the user provided instruction recites "What are the potential risk of joining a vaccine based medical clinical trial in California?".

As previously mentioned, the session identifier in the request 120 can represent a unique identifier that the computer system 122 assigns for the current session of the client device 104, or more generally for interacting with the computer system 122 based on the authentication of the user 102. The user selection status can include an identifier or element index value that specifies an element that is currently selected by the user 102 on the display of 109 for example, the client device 104 can identify one or more selections made by the user 102, e.g., that the user selected a code response, visualizations, and reasonability. The client device identifier can include data that identifies the client device 104 that transmitted the request 120, such as a MAC address, an IP address, an E-mail address, or other identifying information.

In stage (C), the computer system 122 receives the request 120 from the client device 104 over the network 103. In response to receiving the request 120, the computer system 122 extracts data from the request 120. For example, the computer system 122 extracts data from the request 120 retrieve, the session identifier, the user selection status, the client device identifier, and the query 121 provided by the user 102. With this information, the computer system 122 can identify which client device sent the request and whether a session for this device and slash or user is active. Moreover, the computer system 122 can analyze the text input and the user selection status for the type of data to be provided along with the natural language response. The computer system 122 can analyze the user selection status to determine which user interface elements about the interface of display 109, if any, were selected at the time the user 102 interacted with the user interface element 111. If so then the computer system can either limit or augment the natural language response using the selected elements on the interface of the display 1:09, so that other non-selected items are excluded from the processing to generate the additional information. For example, if the user 102 has selected visualizations, e.g., a chart and a table, the computer system 122 can ensure that these selected visualizations will be produced and provided in the natural language response. Additionally, the computer system 122 can use the selections to determine what functions are to be supplied.

In some implementations, the computer system 122 can analyze the data provided in the instruction from the client device 104. For example, the computer system 122 can use one or more natural language processing (NLP) techniques to analyze the natural language query. The NLP techniques can parse the words in the natural language query, identify the meaning of each parsed word in the natural language query, perform semantic analysis on each of the words individually and collectively in the natural language query, identify synonyms of the words in the query, identify an order of the words in the query, identify a number of words in the query, determine a contextual meaning of the query, and perform other functions associated with analyzing a query.

In stage (D), the computer system 122 can determine whether the received request 120 is similar to one or more prior requests, as stored in the database repository 124. The computer system 122 can include a caching lookup engine for this purpose. In further detail, the caching lookup engine may include one or more software modules, a trained machine learning model, or other deterministic model types. The caching lookup engine can utilize the data produced from the NLP techniques that processed the received natural language query in the request 120 to try to identify similar queries in the data repository of 124. For example, the caching lookup engine can use various techniques to try to identify queries from the prior queries 127 in the database repository that matched to the received query in the request 120 within a threshold. The caching lookup engine may use, for example, string matching, fuzzy matching, vectorization techniques, similarity detection along multiple dimensions, and a trained machine learning model that compares the received query to each query in the prior queries 127.

In some implementations, the caching lookup engine can compare the characteristics of the analyze request determined from stage (C) to data in the query/response insights 134. Based on the results of the comparison of those characteristics, the caching lookup engine can determine whether the received query is similar to one or more prior queries. For example, the characteristics of the received query can include the parsed words in the query, the meaning of each parse word in the query, the semantic analysis of each word individually and collectively in the query, synonyms of the words in the query, the order of the words in the query, the number of words in the query, and the contextual meaning of the query. The caching lookup engine can search for similar characteristics in the query slash/insights 134.

For example, the caching lookup engine may find metadata of prior queries that have similar meanings of each parsed word and similar contextual meanings, with a different number of words and different words in prior queries.

In another example, the caching lookup engine may find metadata of queries that include different words, different meanings of each parsed word, yet similar contextual meanings between queries. In another example, the caching lookup engine may find metadata of queries that include the same words, same meanings of each parsed word, a different order of words from the order of words in the received query, and different contextual meanings between queries.

The caching lookup engine may identify metadata of prior queries that match to the metadata of the received query according to weighted criteria. For example, the computer system 122 may weigh certain metadata higher or lower than others. The contextual meaning of queries and the meanings of each parsed word may include a higher weight then the number of words in the query and the order of words in the query. For example, the computer system 122 may apply a 70% weight to a contextual meaning of a query, a 20% weight to the meanings of each parsed word, a 5% weight to synonyms of the word, a 3% weight to an order of the words and a 2% weight to a number of the words. The caching lookup engine can determine whether one or more prior queries match to the received query based on the metadata and their corresponding weights.

The caching lookup engine can identify prior queries when metadata between the prior queries and the receive query matches within a threshold value. For example, the caching lookup engine can determine metadata of a prior query and metadata of the received query have a weighted score of 90% according to similar contextual meaning of queries (e.g., 70% weight to contextual meaning of queries) and a similar meaning of each parse word (e.g., 20% weight to the meanings of each parsed word). Here the caching lookup engine determines the match is 90% confident. The caching lookup engine compares the 90% confidence to a threshold value of 75%, for example. In response to determining the 90% confidence satisfies the threshold value of 75%, the caching lookup engine determines a prior query match has been found. Alternatively, if the caching lookup engine determines a weighted score is less than the threshold value between the received query and a metadata of the prior query and the caching lookup engine determines that this prior query is not a match. Other examples are possible.

In some implementations, the caching lookup engine can include a trained machine learning model that is configured to determine whether the received query in the received request 120 is similar to one or more prior queries 127. In further detail, the computer system 122 can train the machine learning model using data from the prior queries 127 and data from the prior responses 130. The machine learning model may be trained using one or more training algorithms, e.g., backpropagation and a gradient descent algorithm. For example, the computer system 122 can provide as input each query of the prior queries 127 to the machine learning model. The machine learning model can output data similar to a natural language response. In response, the computer system can provide the data output by machine learning model and the actual response of the prior responses 130 as feedback data to the machine learning model. In this manner, the computer system 122 trains the machine learning model to produce an output query from an input query using the prior queries 127 and their corresponding prior responses 130.

Accordingly, the machine learning model of the caching lookup engine is sufficiently trained when the computer system can provide a query of the prior queries 127 and the machine learning model outputs a core responding response that is similar to the actual response of the prior responses 130. Then, the computer system 122 can provide the received query from the receive request 120 as input to the trained machine learning model. The training machine learning model can output a natural language response. In response, the computer system 122 can compare the natural language response output by the training machine learning model to each response of the prior response is 130. If the computer system 122 determines that the natural language response output by the training machine learning model matches to one or more responses of the prior responses 130, then the computer system 122 can select the one or more matched responses to provide back to the client device 104 for the user 102.

In this manner, the caching lookup engine seeks to identify prior queries that were previously processed by the AI/ML models 128 according to the received query in the receive request 120. Generally, the AI/ML models 128 are likely to produce a similar natural language response for the received query in the received request and the one or more queries in the prior queries 127 that match. Accordingly, the computer system 122 can prevent the additional and likely redundant processing by the AI/ML service provider 126 and instead, provide the similar natural language response from the previously processed query that matches the received query to the client device 104.

If the caching lookup engine determines that the metadata of the received query from the received request 120 does not match to metadata of any of the prior queries 127, then the computer system 122 proceeds to stage (E). Alternatively, if the caching lookup engine determines that the metadata of the received query from the received request 120 does match to at least one query of the prior queries 127, then the computer system 122 proceeds to stage (I).

In stage (E), the computer system 122 determines that the received query in the received request 120 is not similar to any prior query stored in the database repository 124. In response, the computer system 122 prepares to transmit the query to the AI/ML models 128 at the AI/ML service provider 126. However, the computer system 122 can perform any type of additional analysis to identify relationships, statistical measures, and other functions related to the request 120 to guide the AI/ML models 128 in generating a natural language response relevant to the national language query.

For example, the analysis performed may include data processing operations that the AI/ML model 128 is unable to perform, or is unable to perform deterministically or as accurately as a dedicated function. In addition, some analysis can include types of functions that are different from or go beyond the processes able to be performed by the AI/ML models 128 such as, for example, querying study clinic databases, identifying clinical trial information, and preparing visualizations associated with the query in the receive request. As a result, the computer system 122 can generate various analysis data, for use by the AI/ML models 128 in generating output.

In some implementations, the computer system 122 can use various models to perform its analysis and generate resultant data. The models can include non-AI/ML models, e.g., software for creating visualizations, software for executing DBMS requests on the data in the database repository 124, and ML models, e.g., mathematical models, statistical models, and trend models, to name some examples. For example, some of the non-AI/ML models can include a query rules engine transformer, a query prediction engine, a database definition language (DDL) helper engine, and other engines.

In some implementations, the query rules engine transformer can generate one or more queries for querying the database repository 124. The query rules engine transformer can analyze the query 121 from the request 120 and generate relevant queries for querying the database repository 124. The query rules engine transformer may include one or more ML models or other models that can predict the types of queries relevant to the query 121 and generate those queries in the relevant software language. In further detail, the query rules engine transformer can generate, from the natural language question in the query 121, one or more relevant queries for querying the database repository 124. These relevant queries can be based on the content of the query 121, predictions of the type of information the user 102 may be seeking with the query 121, and formatted in a manner to retrieve results from the study date of 135, for example. These queries may include filter data types, aggregation of data across different data types, querying for a specific data component, averaging data, and other types of functions associated with querying DBMS.

For example, the computer system 122 can determine that additional data would enhance or supplement the results of the request 120. In some cases, the computer system 122 can determine that additional information from the database repository 124 would aid in responding to the requests of the user 102. For example, the query of the request 120 may ask for specific clinical trial data that the AI/ML models 128 are unable to ascertain. As a result, the computer system 122 can determines that information from the study data 135 would offer data beneficial to the AI/ML models 128 in responding to the request 120. In the example of system 100, the computer system 122 can determine that the AI/ML models 128 may not have access to information related to vaccine based medical clinical trials in California. Accordingly, the query rules engine transformer can query the study data 135 for data related to vaccine based clinical trial in California. The results of the query may include, for example, identification of patients involved in the clinical trial, type of vaccines administered in clinical trial in California, relevant dates of the clinical trial, adverse effects of the vaccines administered to the individuals at the clinical trial, minor symptoms of these vaccines at the clinical trial, and users who managed the clinical trial in California. Other queries are also possible.

The computer system 122 can also predict other types of requests that the user wanted to may ask for in subsequent requests. For example, the computer system 122 can query the database repository 124, and specifically, the study data 135, the prior queries 127, and the prior responses 130, and determine if similar information has been queried in the past by other users. This does not necessarily have to match to the same request or similar requests from stage (D) but the computer system 122 can look for similar content that can aid in predicting subsequent requests by the user 102. If the computer system 122 identifies similar requests or identifies content in this study data 135 that is relevant to the content of the request 120, then the computer system 122 can retrieve that data from the database repository 124 to be incorporated into a request sent to the AI/ML models 128.

In some implementations, the computer system 122 can include a database DDL engine. The database DDL engine formats data retrieved from the database repository 124 into a manner that is more understandable by the AI/ML models 128. For example, when data is retrieved from the study data 135, the computer system 122 retrieves the data in an SDTM format, which is the data format for human clinical trial data tabulations and for non-clinical study data tabulations. However, if the computer system 122 provides the data in the SDTM format to the AI/ML models 128, the AI/ML models 128 may be unable to discern this data type. As a result, the AI/ML models 128 may hallucinate or generate fake answers provided in the AI/ML model output 131.

To prevent this issue, the database DDL engine can modify data retrieved from the study data 135 to be more readable and understandable by the AI/ML models 128. This can include, for example, adding variable names and descriptions to objects retrieved from the study data 135, describing the contents of the columns and rows of data if the SDTM format is returned in a table or chart, for example, and providing context that describes the information displayed in the SDTM data structures.

The database DDL engine can include one or more machine learning models and one or more rule-based engines that are configured to provide description for data in the SDTM format. The database DDL engine is configured and/or trained to analyze the SDTM format and add descriptions, narratives, tags, and other exposition content that elaborates on the data shown in the SDTM format. In this manner, the database DDL engine improves processing of the AI/ML models 128 and reduces the likelihood that they misunderstand the data in the SDTM format.

In some implementations, the computer system 122 can analyze the request and determine that one or more visualizations would be helpful in responding to the request 120 of user 102. The visualizations can include one or more charts, graphs, tables, videos, and others. The computer system 122 can analyze prior queries 127, prior responses 130, the corresponding metadata, and the study data 135 to predict whether visualizations would be helpful in responding to the request 120. For example, the computer system 122 determines whether visualizations were provided to previous users from similar query types. If the computer system 122 determines that one or more prior query types similar to the current query requested for visualizations, then the computer system 122 may predict that the user 102 may like to view visualizations associated with the responses. In another example, the computer system 122 may identifies feedback from users that requested for visualizations after the computer system 122 had provided responses to their queries. In this example, these users may have realized after they reviewed the computer system 122's responses that they prefer visualizations to accompany the responses. Accordingly, the computer system 122 can capitalize on similar query and response types and provide visualizations in the responses when certain users, such as user 102, do not request for visualizations in the initial request.

The computer system 122 can include one or more software modules to prepare the visualizations to provide to the user 102. For example, the computer system 122 can retrieve the data in the database repository 124 to produce the visualizations. This data can be extracted and incorporated into the request to provide to the AI/ML models 128, in order for the LLM to narrate or describe information associated with the visualizations, highlight important features of this data, and tag features relevant to the user 102 in a narrative form.

In some implementations, the computer system 122 can include one or more algorithms that predict future data for the study data 135. For example, continuing with the query provided by the user 102, the computer system 122 can include one or more ML models, such as forecasting model or trend models, which are trained to predict future sequences or series of data, such as future events, future trends, or future outcomes. In the example of system 100, this may include potential future risks for involving themselves in a clinical trial for vaccines in California. The computer system 122 can train one or more ML models on the data in the prior queries 127, the prior responses 130, and the study data 135 to make inferences and or predictions by leveraging statistical analysis, patterns, and various trends, about future data types. The computer system 122 provides as input to the one or more trained ML models data from the query and outputs future sequences or series of data associated with the query. The computer system 122 can incorporate the future sequences or series of data in the request to provide to the AI/ML models 128.

In stage (F), the computer system 122 generates and transmits a request 125 for narrative or descriptive content from the AI/ML models 128. The request 125 can include, for example, the query 121, the formatted data 140, and any metadata 150 associated with the query 121 and the formatted data 140. As mentioned above, the query 121 may include the question answered by user 102 in the text box 110. The formatted data 140 can include data associated with, for example, visualization information generated for the request 120, queried information retrieved from the database repository 124 associated with the request 120, modifications to the query 121 to prevent the AI/ML models 128 from hallucinating, cost information for paying the AI/ML models 128 for processing the request 125, and other information. In addition, the formatted data 140 can also include requests for the model to create software instructions for generating the response to the request 125, stylistic responses for responding to request 125, e.g., professional response, terse response, persuasive responses, and other, and reasoning or thoughts produced by AI/ML models 128 in creating the response to the request 125.

In some cases, the computer system 122 may determine the query 121 includes problematic language that is likely to cause the AI/ML models 128 to hallucinate. The computer system 122 can determine this based on the comparison of the query 121 to one or more prior queries that also caused the AI/ML models 128 to hallucinations. Accordingly, before the received subsequent query is forwarded to the AI/ML models 128 for processing, the computer system 122 can modify the received subsequent query, e.g., clarify the language of the query, add more details to the query, or remove ambiguous words, to name some examples. This can include, for example, reorganizing the wording of the query 121, changing the word of the query 121 using various synonyms, adjusting semantics of the query 121, and removing certain words.

In some implementations, the request 125 can include information selecting a particular AI/ML model of the AI/ML models 128. If the request 120 does not include data identifying a particular AI/ML model, e.g., LLM, to process the query 121, then the computer system 122 may select a particular LLM for processing. If the computer system 122 decides not to select an LLM for processing, then the AI/ML service provider 126 can select a particular LLM for processing. The computer system 122 may determine which LLM is best for processing a current request using the prior queries 127 and the prior response 130. Here, the computer system 122 identifies types of prior queries that are similar to the received query, e.g., similar domain types. The LLM that was used to process the identified prior queries is selected for the received query if that LLM provided prior responses that were not hallucinated and if the user indicated the results were favorable.

The request 125 can combine the query 121, format data 140, and the metadata 150 into a single message or data structure to transmit to the AI/ML service provider 126. This combination incorporated into a single data structure allows the computer system 122's instruction for generating a description or narrative content to produce enhanced or supplemental content that correspond to the request 120 provided by the user 102. Thus, the request 125 includes information to cause the AI/ML models 128 of the AI/ML service provider 126 to generate a narrative, e.g., a description, an explanation, an interpretation, or translation, of the information included in the request 125. The computer system 122 may also select one or more of the AI/ML models 128 to process the request 125. The computer system 122 guides the AI/ML models 128 to provide a description that corresponds to actually answer the query in the request 120 provided by the user 102. As discussed above, regarding the 128 to provide a description includes not only responding to the query 121 but also narrating or describing visualization data included in the format data 140, as well as producing a description in line with criteria from the format data 140. In some cases, the metadata 150 can be used by the AI/ML models 128 to properly generate a response to the request 125. By incorporating the additional information in the request 125, such as the format data 140 and the metadata 150 which significantly aid the AI/ML models 128 in responding to the query 121, the computer system 122 can assist the AI/ML models 128 to generate high quality output that is not only accurate but also aided with result data produced by the computer system 122.

Generally, the request 125 can be used to cause the AI/ML models 128 to produce narrative content that describes or provides narrative text that indicates the most important or prominent relationships, features, and characterizations for responding to the query 121 in the request 120. Often, the data shown in the visualizations and other content may include significant importance that is not apparent to the user 102. Many individuals reviewing their responses produced by the AI/ML models 128 may not correctly interpret results presented to them or may not understand trends or potential predictions produced by the computer system 122. Additionally, the results produced for the user 102 may include an abundance of information that is not easy to parse through for the user 102. In this manner, by allowing the AI/ML models 128 to narrate and describe relevant information indicated by the computer system 122, the computer system 122 can provide enhanced content for the user 102 based on the query 121 alone.

As mentioned, the request 125 can include the metadata 150, the query 121, and the format data 140. The computer system 122 can transmit or provide the request 125 to the AI/ML service provider 126 over the network 103. The AI/ML service provider 126 can provide the AI/ML models 128, such as the LLMs, to access and process the data in the request 125.

In some implementations, the functions or processes described in stages C through L maybe performed by one or more different components in the computer system 122. These different components in the computer system 122 can perform these tasks or functions individually. In this manner each of the different components may perform these tasks in parallel, which reduces the overall processing time, improves the management of these tasks, and ensures that one task is not a bottleneck to another task.

In stage (G), the AI/ML service provider 126 receives the request 125 and generates output 131. The AI/ML service provider 126 can extract the data from the request 125, e.g., extract the stored query 121, the stored metadata 150, and the format data 140. The AI/ML service provider 126 can provide the extracted data as input to one or more of the AI/ML models 128 to generate the enhanced content. The enhanced content may include, for example, a narrative description or textual explanation according to the query 121 and the metadata 150, along with the data interpreted by the metadata 150. In response, the AI/ML models 128 generates the AI/ML model output 131 that includes the narrative description or the textual explanation, as requested for by the user 102.

In some implementations, AI/ML models 128 process the data from the request from 24 to interpret the meaning of these data types and generate the narrative content. Generally, and LLM used to generate a narrative in the form of a natural language response, e.g., response that is human readable, by analyzing various patterns across vast amounts of data in different data types. The LLM can generate a coherent and contextually appropriate narrative of the extracted data from the request 125. In some cases, the LLM can provide summaries of the extracted data from the request 125. In some cases, the LLM can Generate a response in a designated language specific in the request 125, which can correspond to the language of the user 102 or another language, such as English, French, Italian, or other.

The LLM can create the AI/ML model output 131 with characteristics specified by the data in the request 125. For example, the LLM may format the output of narrative text in a persuasive format, a tabular or bulleted format, and/or personalize the narrative text according to preferences of the user 102. In some cases, the LLM can use the format data 140 to interpret or understand contextual information from the metadata 150 and or the query 121. This can include understanding the query 121 asks for data specified by the format data 140 or color-coding certain words in the narrative text.

In some implementations, the AI/ML service provider 126 transmits the AI/ML model output 131 to the computer system 122 over the network 103. In some implementations, the AI/ML service provider 126 transmits the AI/ML model output 131 to the client device 104 over the network. The computer system 122 can intercept the AI/ML model output 131 sent to the client device 104 prior to arriving at the client device 104. In this implementations, the computer system 122 can perform additional processing on the AI/ML model output 131 prior to the output being forwarded to the client device 104.

During stage (H), the computer system 122 can receive the AI/ML model output 131 from the AI/ML service provider 126. The computer system 122 associates the AI/ML model output 131 with the query 121 provided in the request 120. In some cases, the computer system 122 can generate data that associates the AI/ML model output 131 with the query 121. The associated data can include, for example, an index, an address, or a pointer that references the output 131 with the query 121. Using the associated data, the computer system 122 can store the AI/ML model output 131 in the prior responses 130 in the database repository 124 and the query 121 in the prior queries 127.

Moreover, the computer system 122 can store the data associating the AI/ML model output 131 with the query 121 in the metadata should have the database repository 124. The metadata may also include, for example, the software instructions produced by the AI/ML models 128, descriptions of any visualizations requested for by the computer system 122, timestamp data associated with the AI/ML models 128 that produced the AI/ML model output 131, a version number of the AI/ML models 128 that produced the AI/ML model output 131, a selected one of the AI/ML models 128 that processed the request 125, and any other information output by the AI/ML models 128.

Returning to stage (D), if the caching lookup engine determines that the metadata of the received query from the received request 120 does match to at least one query of the prior queries 127, then the computer system 122 proceeds to stage (I). During stage (I), the computer system 122 can retrieve results associated with the match query of the prior queries 127. In some cases, if the computer system 122 determines that the received query 121 from the received request 120 matches to two or more prior queries 127, then the computer system 122 grabs each response from the prior responses 130 in the database repository 124 associated each of the matched queries.

During stage (J), the computer system 122 can determine whether additional analysis is needed. For example, the computer system 122 can validate the AI/ML model output 131 before providing to the client device 104. The computer system 122 can validate, clean, or correct any HTML, JavaScript, Python, SQL, or any other content from the AI/ML model output 131, to name some examples. Moreover, the computer system 122 can determine whether the AI/ML service provider 126 generated the narrative content or description consistent with the criteria provided in the request 125. In some cases, the computer system 122 can validate any markup language content or code provided in the AI/ML model output 131 to ensure that it does not present a security risk for the 126, the computer system 122, or the client device 104.

In some cases, the computer system 122 can analyze any visualizations to determine whether any issues exist with such visualizations. This can include not readable plots, misused color scheme, and other issues with the visualizations. If the computer system 122 determined issues exist with the visualizations then the computer system can rerun the visualizations using either the AI/ML models 128, any local functions at the computer system 122, or other.

Moreover, the computer system 122 can perform additional verifications to determine whether the user 102 would benefit from additional visualizations, descriptions, features, and other components not currently found in the AI/ML model output 131 or in a prior response selected from the database repository 124. The computer system 122 may perform functions associated with visualizations, adding additional descriptions, or adding reasonability features not currently found in the response. However, the computer system 122 may add this information only if the computer system 122 predicts the user wants who would benefit from this information. For example, if the computer system 122 determines the user has provided feedback in the past for additional information, e.g., visualizations and readability descriptions, then the computer system 122 is more likely to add the additional analysis to the response.

In some implementations, the computer system 122 can include a query prediction engine. The computer system 122 can utilize the query prediction engine to determine a subsequent query or queries the user 102 is likely to ask for after reviewing the response data 142. The query prediction engine can include one or more trained ML models that can analyze a current query 121 and response data 142 in order to determine a subsequent query the user 102 is likely to ask for next.

For example, the query 121 includes the question of "What are the potential risks of joining a vaccine based medical clinical trial in California?". The response data 142 can include, as illustrated in system 100, an answer to the question, the code response, visualizations, and reasonability. The query prediction engine can analyze this information and determine that the next question the user is likely to ask is "How do I join the vaccine based medical clinical trial in California?" In this instance, the query prediction engine can recommend this question and transmit this question along with their response data 142 to the client device 104. Now, the user 102 already has a potential next question along with the results of the initial query 121.

The query prediction engine can recommend other questions as well. The user may decline the questions which can be provided as feedback for improving the query prediction engines predictions. Similarly, if the user accepts the recommended question provided by the query prediction engine pick karma this feedback can also improve the query prediction engines confidence in its outputs.

In some implementations, the computer system 122 can determine whether the AI/ML models 128 hallucinated the AI/ML model output 131. Hallucination refers to the generation of plausible sounding but fundamentally and factually incorrect information produced by the AI/ML models 128, e.g., the LLMs. In further detail, an LLM hallucinates when the model generates text as output that appears coherent and accurate but contains factual inaccuracies, fabrications, or results with inconsistencies. The computer system 122 can check the AI/ML models output 131 by utilizing the software produced by the AI/ML models 128 on the local data in the database repository 124. For example, the AI/ML service provider 126 can provide not only the response to the query 121 in the AI/ML model output 131, but also the software instructions utilized by the AI/ML models 128 to produce the response to the query 121. Here, the software instructions may be, for example, Python code, Java code, C++ code, or any other desired language.

The computer system 122 can verify whether the AI/ML models 128 hallucinated by executing the received software instructions using the data from the study data 135 and a local compiler. The computer system 122 can access execute the software instructions locally, which may access data from the study data 135 as necessary, and produce an output from the execution. In response to executing the software instructions and producing the output from the execution, the computer system 122 can compare the locally produced output to the AI/ML model output 131. If the computer system 122 determines the output is the same, then the computer system 122 can determine that the AI/ML models 128 is not hallucinating, and proceeds to stage (K).

However, if the computer system 122 determines the output is different, then the computer system 122 can notify the client device 104 that the AI/ML models 128 is hallucinating. In some cases, the computer system 122 may not be able to execute the software instructions produced by the AI/ML models 128, because the software may be incoherent, may include errors that break the compiler, or may generally not execute against the study data 135. In this instance, the computer system 122 may provide feedback to the AI/ML service provider 126 indicating that the AI/ML models 128 are hallucinating using the query 121 for retraining purposes.

During stage (K), the computer system 122 prepares to send response data 142 to the client device 104. The response data 142 can include either the results retrieved from one or more prior responses 130, the AI/ML model output 131 produced by the AI/ML models 128, and any additional analysis determined from stage (J). Prior to sending, the computer system 122 can store the generator response data and the request 120 in the database repository 124.

During stage (L), the computer system 122 generates and transmits response data 182 to the client device 104 over network 103, where the response data 142 can include or be derived from the AI/ML model output 131. The computer system 122 can utilize the client device identifier, the session identifier, and any other necessary information in the request 120 to transmit the response data 142 to the appropriate client device 104. This is important when the computer system 122 services multiple client devices at a time.

In stage (M), the client device 104 receives the response data 142 and displays it for the user 102. The client device 104 can present the response data 142 as part of the results in responding to the query provided in the text box 110 during stage (A). The response data 142 can include text, images, markup language content, code, videos, charts graphs, and any other information. The client device 104 can display the response data 142 in the same display window, e.g., display 109, as the entered question provided by the user 102.

The system 100 can repeat the process discussed above for stages (A) through (M) each time user 102, client device 104, or computer system 122 triggers the creation of a query being processed and a response to be displayed on the client device 104. Additionally, the process of stages (A) through (M) can be performed independently and in parallel to provide different responses for each of multiple different client devices that each have provided their own queries to the computer system 122.

Figure 2:
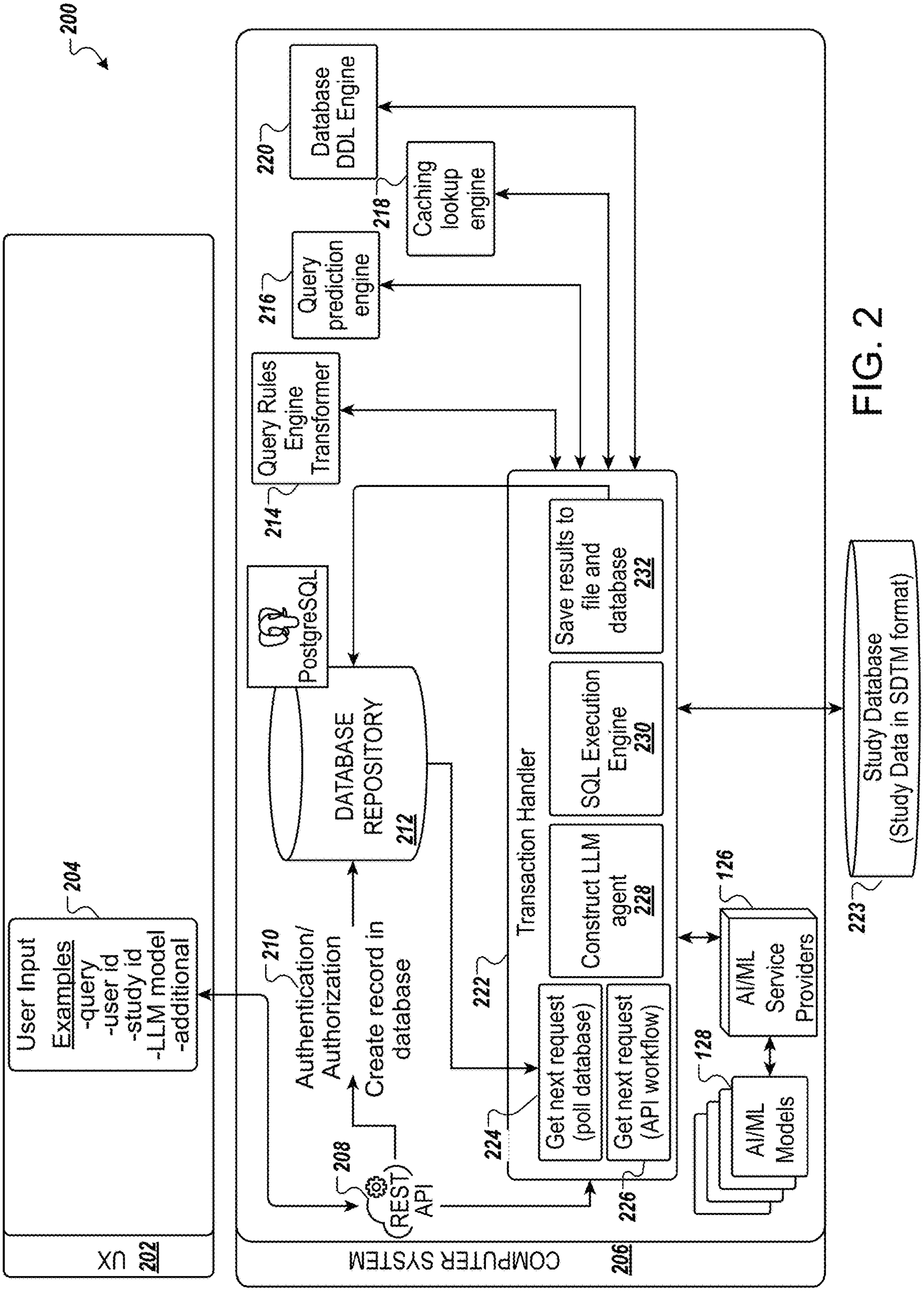
FIGS. 2 and 3 are diagrams illustrating examples of a computer system that provides enhancements to the communications between the user device and the one or more AI/ML models.

FIG. 2 is a diagram illustrating an example of a system 200 that provides enhancements to the communications between the user device and the one or more AI/ML models. The system 200 illustrates similar components shown from system 100 of FIG. 1, including the client device 104, the computer system 122, and the AI/ML service provider 126.

For example, the system 200 includes a client device, such as client device 104, that displays a user interface 202. The user interface 202 allows the user to input this information for communicating with the AI/ML models 128. This user input 204 can include, for example, a query, a user ID, a study ID, a particular LLM model, and additional information. The client device 104 can transmit the user input 204 to the computer system 206.

In some implementations comma the computer system includes a REST API 208. The REST API 208, which stands for representational state transfer application programmable interface, is an API that conforms to the design principles of the REST architectural style. The REST API 208 provides for applications and services to connect components in a microservices architectures. At 210, the computer system 206 authenticates and or authorizes the user of client device 104 using the user input 204. The computer system 206 may authenticate or authorize the user using a username and/or password. Upon successful authentication or successful authorization, the computer system 206 can store a record of a session for that user in the database repository 212.

In some implementations, the computer system 206 may include a transaction handler 222, a query rules engine transformer 214, a query prediction engine 216, a caching lookup engine 218, and a database DDL engine 220. The computer system can include other components that enable communication with the AI/ML service provider 126 and the client device 104. The transaction handler 222 can communicate with a study database 223. In some cases, the study database 223 may be external to the computer system 206.

The study database 223 can be an extension of the data stored in the database repository 212. For example, the components of the computer system 206 can query both the database repository 212 and the study database 223 for information. Moreover, the transaction handler 222 can communicate with the AI/ML service provider 126 that manages the one or more AI/ML models 128.

In some implementations, the query rules engine transformer 214 can generate one or more queries for querying the database repository 212. The one or more generated queries can include queries relevant to the query received from the user 102. For instance, the query rules engine transformer 214 can generate the natural language question of the query received from the user 102 into one or more queries in a particular software language, e.g., SQL, for querying for data from the database repository 212.

In some implementations, the query prediction engine 216 includes one or more trained ML models to recommend one or more subsequent queries the user is likely to ask. In further detail, the query prediction engine 216 can determine one or more subsequent queries the user is likely to ask in response to reviewing response data to a current query. The query prediction engine 216 can provide the one or more subsequent queries to the client device 104 for the user's review. The query prediction engine 216 can improve their processing based on negative and positive feedback provided by the user on the recommended queries.

In some implementations, the caching lookup engine 218 can include one or more software modules, trained ML models, or other model types trained to determine whether the request received from the user is similar to one or more prior requests, as stored in the database repository 212. The caching lookup engine 218 can utilize various techniques to try and identify one or more prior queries in the database repository 212 that matches to or matches to a degree of the received query. The caching lookup engine may utilize, for example, string matching, fuzzy matching, vectorization techniques, and a trained machine learning model that compares the received query to each query in the prior queries to identify matches.

In some implementations, the database DDL engine 220 can include one or more trained ML models one or more rule-based engines that are configured to provide additional description for data stored in the study database 223. For example, the database DDL engine 220 can format data retrieved from the database repository 212 and the study database 223 into a manner that is more understandable and readable by the AI/ML models 128. For example, the database DDL engine 220 can add variable names and descriptions to objects retrieved from the study database 223, describe the contents of the columns and rows of data if the SDTM format is returned in a table or chart, for example, and provide context that describes the information displayed in the SDTM data structures. Moreover, the database DDL engine 220 can add descriptions to any data retrieved from the database repository 212 that is to be subsequently provided to the AI/ML models 128.

The transaction handler 222 manages the transactions from each client device and the AI/ML service providers 126. In some implementations, the transaction handler 222 includes a function 224 for getting a next request (poll database), a function 226 for getting a next request (API workflow), a function for constructing the LLM agent 228, an SQL execution engine 230, and a function for saving results to file and database 232.

The function 224 for getting the next request by polling the database repository 212 includes the transaction handler 222 polling, on a periodic basis, the database repository 212 for any requests received from various client devices that communicate with the computer system 206. When a client device transmits a request to the computer system 206, the request is stored in the database repository 212. The transaction handler 222 can periodically poll the database repository 212 for the request or the transaction handler 222 can retrieve the request from the database repository 212 each time a new record is created in the database repository 212.

The function 226 for getting the next request according to the API workflow includes the transaction handler 222 getting a request through the REST API 208. This can include, for example, receiving various requests from client devices, e.g., initial requests, feedback, and subsequent requests from the same client device, and other information from the client devices.

In some implementations, the transaction handler 222 may construct an LLM agent in 228 of the AI/ML models 128. The LLM agent can include one or more instantiations of the AI/ML models 128, such as the LLM. The transaction handler 222 may construct the LLM agent by applying the LLM of the AI/ML models 128 to a framework that allows for users and or other components to interact with the LLM agent. The LLM agent can perform tasks and make decisions based on the input, similar to the AI/ML models 128.

In some cases, when the transaction handler 222 instantiates the LLM of the AI/ML models 128 as an agent, the LLM is integrated into the computer system 206 such that the LLM agent can manage various interactions, process inputs, and manage other tasks, such as querying databases connected to the computer system 206. For instance, the transaction handler 222 can embed the LLM agent in software that allows the LLM agent to be versatile, e.g., allowing for it to fetch data, perform calculations, maintain memory across various interactions, maintain track of context across interactions and provide more relevant responses. Generally, the LLM agent can allow for the capabilities of the LLM of the AI/ML models 128, while adding additional layers of functionality associated with the computer system 206. In some cases, the computer system 206 may directly communicate with the AI/ML models 128 instead of constructing the LLM agent in 228.

In some implementations, the transaction handler 222 may include an SQL execution engine 230. The SQL execution engine 230 may include one or more software components that convert any requests for retrieving data from the study database 223 into an SQL software instruction for querying the study database 223. The SQL execution engine 230 can receive a request for communicating with the study database 223, such as from one of the query rules engine transformer 214, the query prediction engine 216, or other, transform the request into an SQL instruction for querying the study database 223, and execute the SQL command on the study database 223. The SQL execution engine 230 can produce results from the execution of the SQL command and provide the relevant results to the requesting user or data component. Moreover, the SQL execution engine 230 can store the results in the database repository 212.

In some implementations, the transaction handler 222 can include a function for saving results to file and database 232. The transaction handler 222 can save the output of the LLM agent or the AI ML output from the AI/ML models 128 to a file. In some cases, the transaction handler 222 can save this file to the database repository 212. Additionally, each of the inputs and outputs utilized and produced by the query rules engine transformer 214, the query prediction engine 216, the caching lookup engine 218, and the database DDL engine

220 is saved as a file and stored in the database repository 212. The transaction handler 222 can also store prior queries, prior responses, metadata, e.g., the AI/ML model insights and the query response insights, and user identities, in the database repository 212.

The AI/ML service providers 126 and the AI/ML models 128 is similar to the same components illustrated and described in FIG. 1. More generally, the components described and illustrated in FIG. 2 are similar to the components illustrated and described in FIG. 1.

Figure 3:
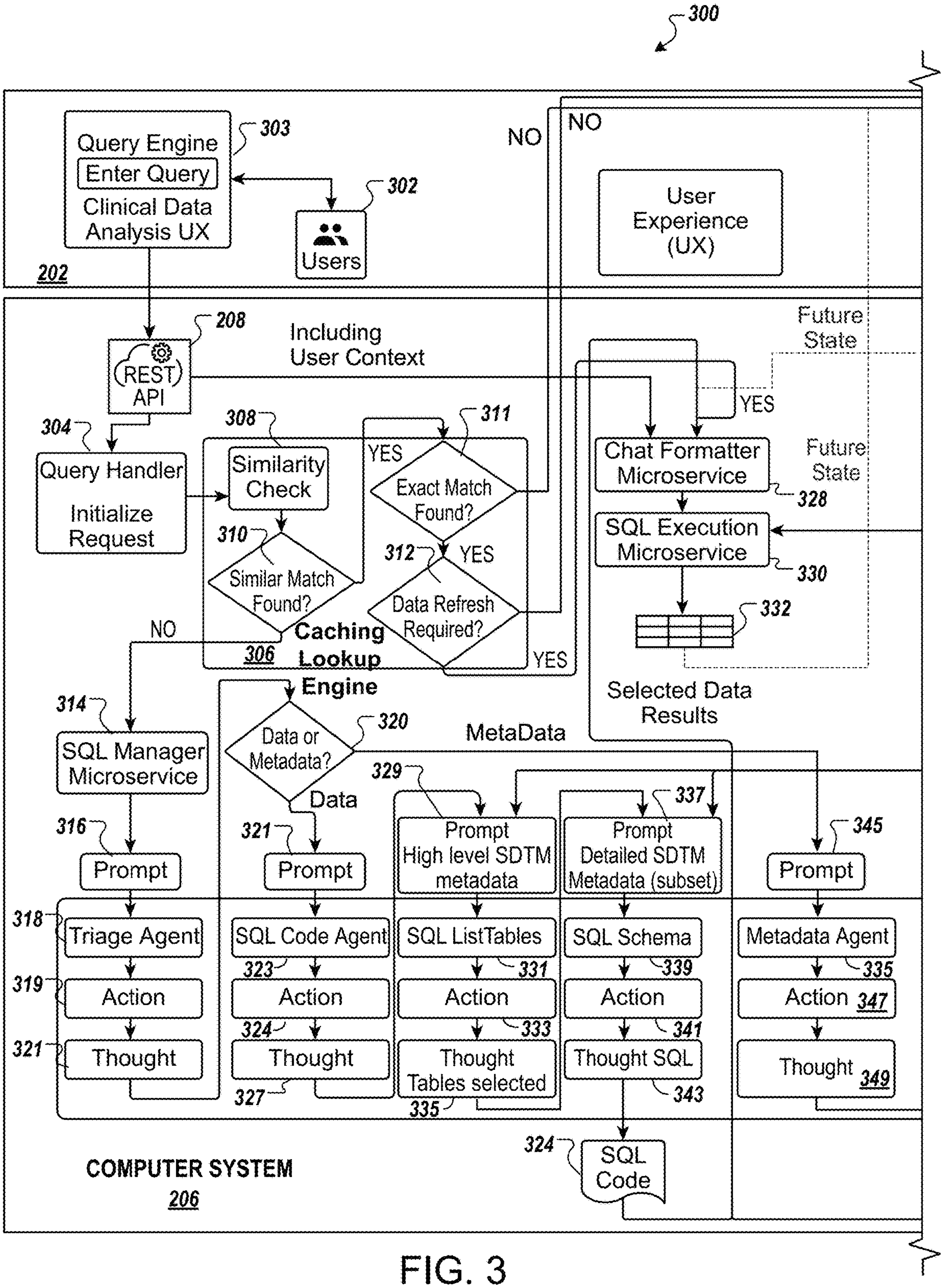
Figure 3:
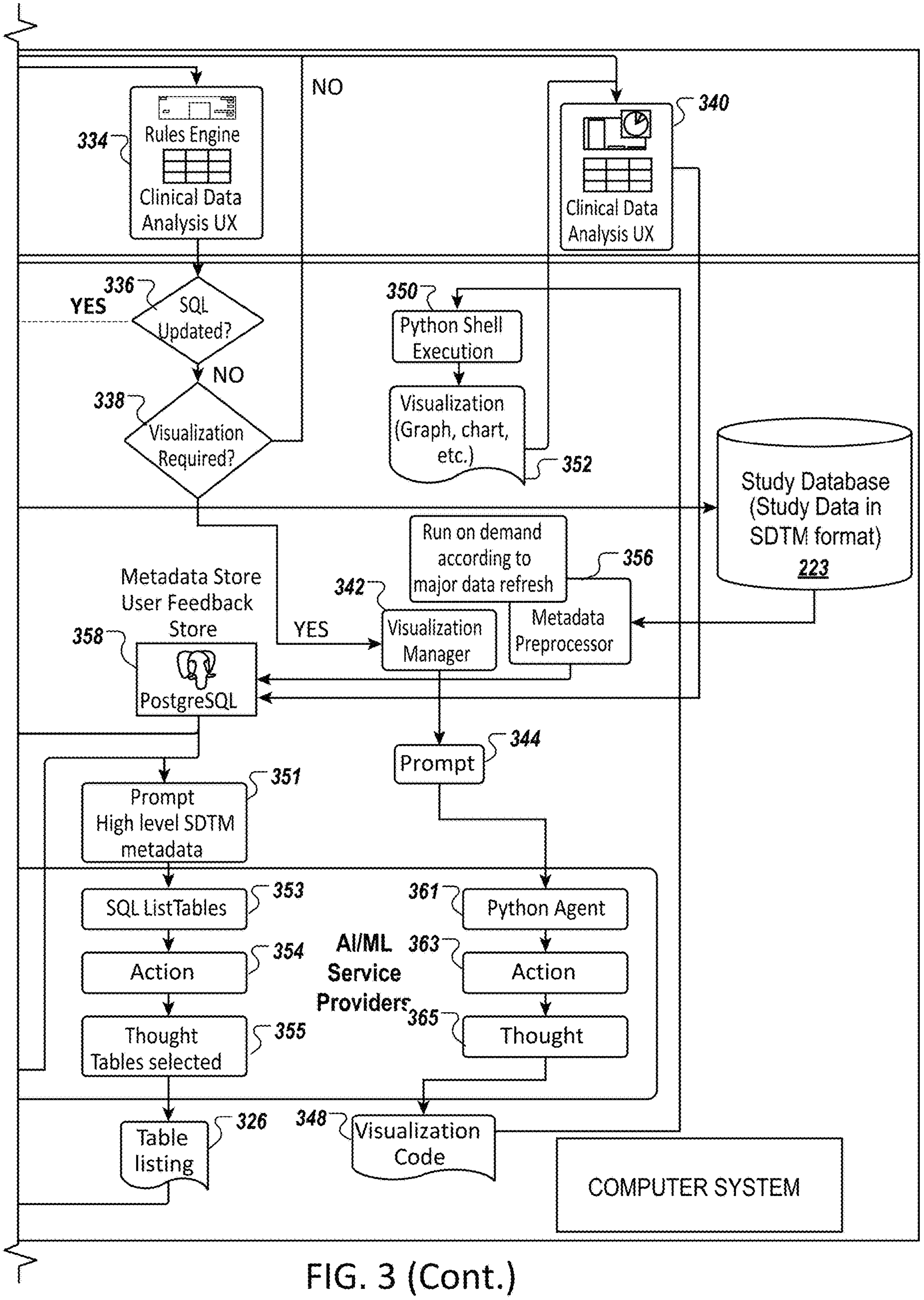

FIG. 3 is a system 300 illustrating an example of a computer system that provides enhancements to the communications between the user device and the one or more AI/ML models. The system 300 illustrates similar components and functions to those shown in the system 200 of FIG. 2 and the system 100 of FIG. 1.

As illustrated in the system 300, a user 302 can input a query into the user interface 202 of the client device 104. The client device 104 can include a query engine 303 that receives the query from the user 302 and prepares to transmit the query to the computer system 206. The computer system 206 can receive the query at the REST API 208 from the client device 104.

The computer system 206 can include a query handler 304. The query handler 304 can initialize the request and provide the initialized request to the look up caching lookup engine 306. The caching lookup engine 306 can perform a similarity check in 308. The similarity checked in 308 can analyze the words of the query in the request, semantics of the query, and other information of the query. Moreover, the similarity checks in 308 can determine whether the receive request is similar to any other prior request received and processed by the computer system 206. At 310, the caching lookup engine determines if a similar match is found. If a similar match is not found then the received query is provided to the SQL manager microservice 314. If a similar match is found, then at 311, the caching lookup engine determines if an exact match was found.

If the caching lookup engine determines an exact match was found at 311, then the process moves to 312, where the caching lookup engine determines whether a data refresh is required a data refresh required. A data refresh is required when the underlying data in the response changes from the prior response. The caching lookup engine can compare the prior response that is associated with the matching request to data stored in the database repository to determine whether their response would be different now. If that is the case, the computer system 206 can perform a data refresh and send the data refresh request to the chat formatter microservice 328. If a data refresh is required, then at 356, the computer system 206 can perform a data refresh. These functions include the computer system 206 retrieving metadata from the study data in the study database 223 and refreshing the data in the data repository.

Returning to 314, the computer system 206 provides the received query to the SQL manager microservice. The SQL manager microservice 314 can format the received query to provide to an LLM agent. At 316, the computer system 206 prompts an LLM agent with the received query. The LLM agent at 318 is a triage agent. The triage agent 318 determines the type of functions that need to be performed associated with the received query. For example, the triage agent 318 determines whether SQL code is to be generated, whether visualizations are requested for and requested to be described, whether Python code is to be generated, and whether metadata is to be analyzed by an LLM agent. Based on the type of functions that need to be performed, the triage agent 318 routes queries to appropriate sub-systems, SQL code agent 323, python agent 361, or metadata agent 335, based on the query type, user context, and similarity detection. At 319, the triage agent 318 can process the prompt from 316. In some cases, the triage agent 318 may be a local LLM agent. In some cases, the triage agent 318 may be located at a separate device, such as the AI/ML service provider 126. The output or thought 321 produced by the triage agent can then be assessed. Output or thought 321 can indicate the type of data to be processed from the received request.

At 320, the computer system 206 determines whether the received request requires processing of data or metadata. If the computer system 206 determines that the received request requires processing of data, then the computer system 206 prompts an LLM agent with the data at 321. The SQL code agent 323 can generate SQL code for processing the request. At 324, the SQL code agent 323 can process the prompt from 321. In some cases, the SQL code agent 323 may be a local LLM agent. In some cases, the SQL code agent 323 may be located at a separate device, such as the AI/ML service provider 126. The output or thought 327 produced by the SQL code agent 323 can then be assessed. Output or thought 327 can indicate the SQL code that is to query the study data in the data repository.

The SQL code output at 327 can be provided to 329, which prompts for high level SDTM metadata. The SQL code output can be processed on the high level SDTM metadata to identify relevant metadata at 329. The output can include various SDTM tables, for example. The SQL ListTables 331 can include an LLM agent, such as a local LLM agent. In some cases, the SQL ListTables 331 may be located at the AI/ML service provider 126. At 333, the SQL ListTables processes the various SDTM tables and at 335, the SQL ListTables selects one or more of the SDTM tables that are relevant.

At 337, the computer system 206 provides the selected one or more SDTM tables, which is a prompt for detailed SDTM metadata. The SQL schema 339 can include an LLM agent, such as a local LLM agent or the SQL schema may be located at the AI/ML service provider 126. At 341, the SQL schema 339 processes the various one or more SDTM tables to produce the SQL code at 343. The computer system 206 can provide the produced SQL code at 324 to the chat formatter microservice 328. The chat formatter microservice 328 formats the SQL code for selecting data in the tables and for providing the SQL code as a response to user query. At 330, the SQL execution microservice executes the SQL code 324 on various tables in SDTM table format in the study database 223. The output 332, e.g., the selected data results from the SDTM data tables, is then provided to the rule engine 334, and through the user interface 202 for user input.

Referring back to 320, if the computer system 206 determines that the received request requires processing of metadata, then the computer system 206 prompts an LLM agent with the metadata at 345. The metadata agent 335 can generate metadata for processing the request. At 347, the metadata agent 335 can process the prompt from 345. In some cases, the metadata agent 335 may be a local LLM agent or located at a separate device, such as the AI/ML service provider 126. The output or thought 349 produced by the metadata agent 335 can then be assessed. Output or thought 349 can indicate the relevant metadata for the received query.

The relevant metadata can then be provided to 351, which prompts for high level SDTM metadata. The relevant metadata is then processed against high level SDTM metadata from the database repository at 351. The SQL ListTables 353 is a similar LLM agent to the SQL ListTables 331. At 354, the SQL ListTables 353 processes the high level SDTM metadata from SDTM tables to find matches to the relevant metadata. At 355, the SQL ListTables 353 selects one or more SDTM tables that include the high level SDTM metadata that match to the relevant metadata. At 326, the computer system 206 selects the table listings in SDTM table format. The table listing 326, is then provided to the chat formatter microservice 328, as similarly described above.

Referring back to 334, the user can interact with the interface to provide updates to the selected data results from the SDTM data tables or to provide updates to the SQL code. In response, at 336, the computer system 206 can determine whether the user requested updates to the SQL code. If the computer system 206 determines the user updated the SQL code, then the computer system 206 provides the updated computer code to the chat formatter microservice 328, and that process repeats.

Alternatively, if the computer system 206 determines that the SQL code is not updated, then at 338, the computer system 206 can determine whether a visualization is required. In some cases, the computer system 206 determines whether the visualization is required based on a response provided by the user at 334. In some cases, the computer system 206 can determine predictively whether the visualization is required based on prior queries, prior responses, and whether the data included in the request would benefit from a visualization. If the computer system 206 determines that a visualization is not required, then the computer system 206 can provide the selected items to the user interface at 340 for the user review.

Alternatively, if the computer system 206 determines that the visualization is required at 338, then the computer system 206 can provide the selected items from the SDTM data tables to the visualization manager at 342. At 342, the visualization manager can analyze the selected items and the type of visualization and generate a prompt for providing as an input to an LLM or LLM agent. The prompt may include an instruction for the LLM to generate software in a particular language, e.g., python or JavaScript, to create a visualization. The python agent 361 can generate python software that when executed by processor creates a visualization. The python agent 361 analyzes the prompt, and at 363, the python agent 361 processes the prompt. The output or thought 365 can include the software instructions in the relevant language produced by the python agent 361 for creating the visualization. The visualization is associated with the relevant items selected from the SDTM tables.

The computer system 206 can provide the visualization code 348 to the python shell execution 350. The python shell execution 350 can execute the visualization code 348 to produce the visualization 352. For example, the python shell execution 350 can include a python compiler that can execute the visualization code 348 in python to produce the visualization 352. The visualization 352 may include, for example, a graph, a chart, a video, a table, or another form of visualization. The output visualization can then be provided to the user interface at 340 for the user review.

In some implementations, the user interacting with the user interface 202 can provide feedback. The computer system 206 can receive feedback on responses and validations, and leverage the feedback to refine future outputs and improve query handling. The feedback can include, for example, changes to the visualizations, changes to the selected SDTM items, changes to the SQL code, and changes to the responses to the query, to name a few examples. The computer system 206 can receive the feedback at 358. If there is feedback provided by the user, then the computer system 206 can provide the feedback to the various LLMs. For example, the feedback, which include updates to the metadata, can be provided to (i) the prompt at 351 for high level SDTM metadata, (ii) the prompt at 337 for detailed SDTM metadata, and (iii) prompt at 329 for high level SDTM metadata at 329. These respective processes then repeat.

Referring to 311, if the caching lookup engine determines that an exact match is not found, then the computer system 206 provides the associated response of the similar query to the rules engine 334, through the user interface 202 for user input. Referring to 312, if the data refresh is not required, the computer system 206 provides the response associated with the matched exact query to the user interface at 340.

In some implementations, the processes illustrated in the system 300 may be performed without the use of the rules engine 334. Here, the computer system 206 may determine whether to incorporate visualizations, SQL code, python code, reasonability, and other requests from the initial query provided by the user 302. In some cases, the computer system 206 may include a single LLM agent that can perform each of the functions of the aforementioned triage agent 318, SQL code agent 323, SQL ListTables 331 and 353, the SQL schema 339, the Metadata Agent 335, and the Python Agent. In this manner, the computer system 206 may provide one request to the single LLM agent to perform each of the functions and return the requested data in a single response. Additionally, the LLM agent may be located at a separate device, e.g., AI/ML service provider 126, or located in the computer system 206.

Figure 4:
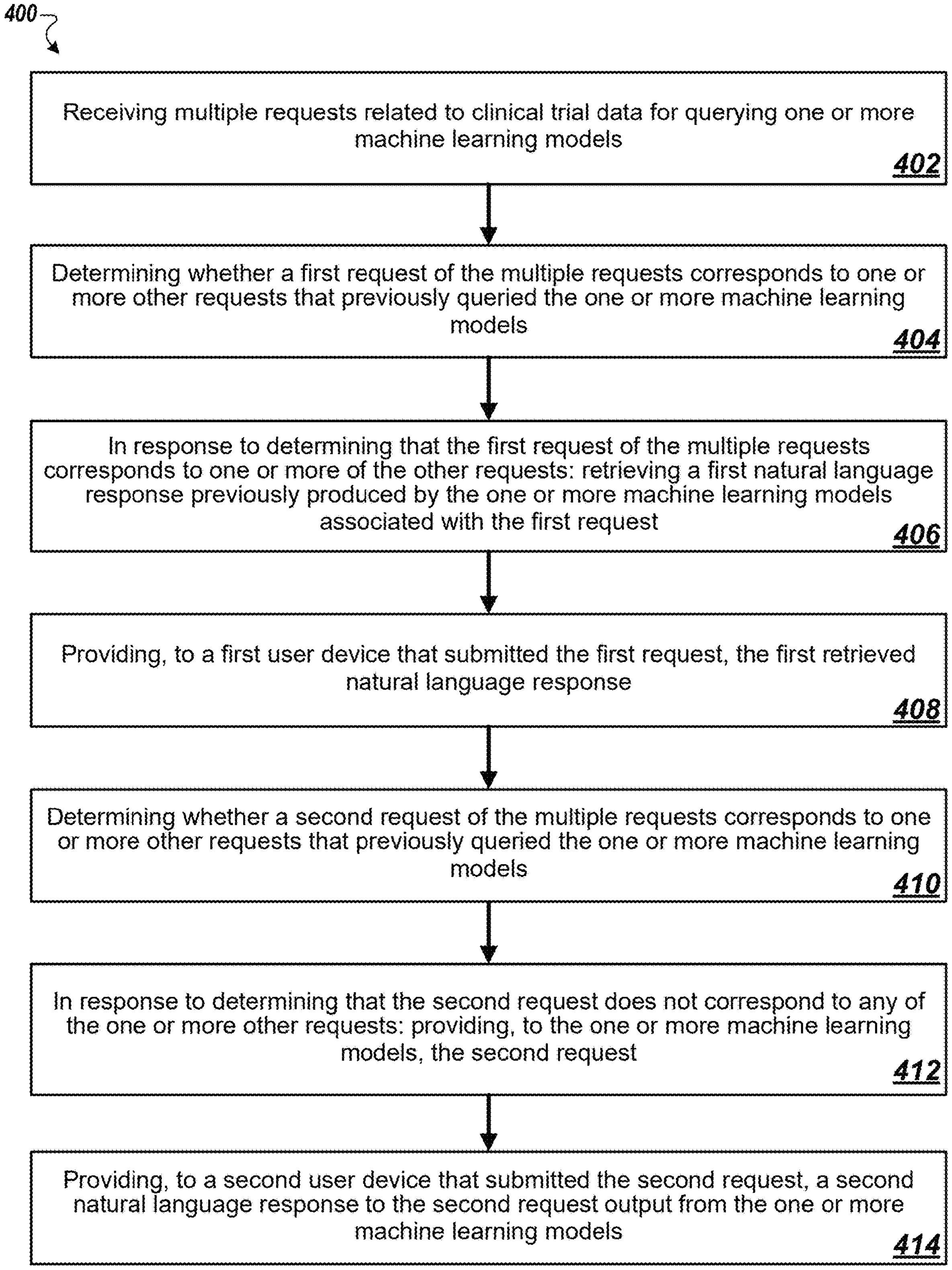
FIG. 4 is a flow diagram that illustrates an example process for enhancing query transactions between multiple user devices and one or more AI/ML models.

FIG. 4 is a flow diagram that illustrates an example process 400 for enhancing query transactions between multiple user devices and one or more AI/ML models. A computer system, e.g., computer system 122 of FIG. 1 or computer system 206 of FIGS. 2 and 3, may perform the process 400.

The computer system receives multiple requests related to clinical trial data for querying one or more machine learning models (402). In some cases, the computer system may receive multiple requests from the same user device or a single user request from a single user device. In some cases, the computer system may receive multiple requests from multiple user devices. In further detail the computer system receives, from the multiple user devices, the multiple requests provided by a respective user through an interface of each user device of the multiple user devices. Each request of the multiple requests includes a natural language question for querying the one or more machine learning models. In some examples, the one or more machine learning models include one or more large language models.

The computer system determines whether a first request of the multiple requests corresponds to one or more other requests that previously queried the one or more machine learning models (404). The computer system analyzes the first request and identifies characteristics of the first request. Specifically, the computer system identifies the characteristics of the first request by parsing words in the first request into separate words. The computer system analyzes these parsed terms to identify a number of parsed words in the first request and using semantic analysis, identifies a meaning of each parsed word in the first request. Based on the meaning of each parsed word and the number of parsed words in the first request, the computer system identifies a contextual domain of the first request.

Using the contextual domain of the first request, the computer system can compare the contextual domain and data types of the first request to one or more other requests that previously queried the one or more machine learning models. The computer system can compare each received request to the one or more other requests that previously queried the one or more machine learning models. In further detail, the computer system accesses a database that stores previous requests and information associated with the previous requests. For instance, the database stores (i) a plurality of other requests that previously queried the one or more machine learning models, (ii) a plurality of natural language responses output by the one or more machine learning models associated with the plurality of other requests, and (iii) metadata associated with each request of the plurality of other requests. The metadata includes, for example, data identifying a plurality of users that interacted with the one or more computers, a timestamp and data associated with each other request of the plurality of other requests, and a contextual domain of each other request of the plurality of other requests.

The computer system can compare each received request of the multiple requests to the previous requests stored in the database. To determine whether the request corresponds to one or more other requests, the computer system can compare the contextual domain of the received request with contextual domain of the previous requests stored in the database and determine whether the comparison between the contextual domain of the received request and the contextual domain of the other request are similar according to a threshold value. If a result of the comparison satisfies the threshold value, the computer system retrieves the other previous request and a natural language response that was produced by the one or more machine learning models from processing the other request. The computer system can use other types of semantic analysis or criteria in performing the comparison between a received request and each other stored requests.

The computer system determines whether the request corresponds to one or more other requests by determining whether the request matches to another request, partially matches to another request, matches to another request using criteria according to a threshold value, or another type of matching or non-matching. In some cases, the computer system can determine whether the request is similar to one or more other requests or dissimilar to one or more other requests.

In some implementations, the computer system can build the database that stores the previous requests and other information associated with the previous requests. For example, the computer system can monitor communications between the multiple user devices and the one or more machine learning models. In further detail, each time a request is sent from a user device to the one or more machine learning models, the computer system can obtain the request and store the request in the database. The one or more machine learning models produces a response to processing the request, and the computer system captures and stores that response with the corresponding request in the database. Moreover, the computer system can generate and store metadata for each request provided by a client device and for each response produced by the one or more machine learning models in the database. The metadata, the request, and the response produced by the one or more machine learning models can be stored in the database in an indexable fashion to allow the computer system to search for this information in the future.

In response to determining that the first request of the multiple requests is similar to one or more of the other requests, the computer system retrieves a first natural language response previously produced by the one or more machine learning models associated with the first request (406). In particular, the computer system retrieves, from the database, the first natural language response associated with the other request that matches to the first request or is similar to the first request.

The computer system provides, to a first user device that submitted the first request, the first retrieved natural language response (408). In further detail, the computer system transmits, over a network and to the first user device, the retrieved first natural language response associated with the other request. In this case, the computer system does not need to query the one or more large language model in determining an answer to first request.

The computer system determines whether a second request of the multiple request is similar to one or more other requests that previously queried the one or more machine learning models (410). The functions performed in (410) are similar to the functions performed in (404).

In response to determining that the second request is dissimilar to any of the one or more other requests, the computer system provides, to the one or more machine learning models, the second request (412). In particular, the computer system transmits, over a network and to the one or more machine learning models, the second request and metadata associated with the second request selected from a database. The one or more machine learning models can process the second request and the metadata associated with the second request to produce output, e.g., a natural language response to the natural language query posed by the data in the second request.

In some implementations, the computer system can provide, to the one or more machine learning models, a request for one or more software instructions utilized by the one or more machine learning models in producing the output for processing the second request. The computer system can receive or obtain the output from the one or more machine learning models that processed the (i) second request and (ii) the request for the one or more software instructions. The output and the one or more software instructions produced by the one or more machine learning models can be stored in the database with data identifying the second request.

The computer system can determine whether the output from the one or more machine learning models is accurate by executing the received one or more software instructions. In particular, the computer system can generate output by locally executing, using one or more processors, the one or more software instructions using data from the database, the one or more software instructions utilized by the one or more machine learning models in producing the output for processing the second request. Based on the execution, the computer system can compare the (i) generated output from locally executing the one or more software instructions received from the one or more machine learning models and (ii) the obtained output from the one or more machine learning models.

In response to comparing the (i) generated output from locally executing the one or more software instructions received from the machine learning models and (ii) the obtained output from the one or more machine learning models, the computer system can provide, to the second user device, data indicative of the obtained output that processed the second request in response to determining the generated output is similar to the obtained output.

In some implementations, in response to performing the comparison, the computer system can determine whether the generated output is dissimilar to the obtained output from the one or more machine learning models or determine whether the local execution of the one or more software instructions received from the one or more machine learning models is unable to be executed. If either of these conditions are true, the computer system can provide, to the second user device, data indicating that the one or more machine learning models cannot process the second request.

The computer system provides, to a second user device that submitted the second request, output from the one or more machine learning models that processed the second request (414). In particular, the computer system receives, from the one or more machine learning models, the output produced by the one or more machine learning models from processing the second request and the metadata. The computer system transmits, over a network and to the second user device, the output produced by the one or more machine learning models from processing the second request and the metadata.

In some implementations, the computer system can determine that a third request of the multiple requests is similar to the one or more other stored requests within a threshold value. For example, the computer system may determine the third request may be similar, and within the threshold value, to one or more other stored requests according to a semantic analysis, word types, and other information types. However, the computer system may determine that the third request is similar to another request that caused the one or more machine learning models to hallucinate or that the third request can be improved using data from the similar request to obtain an improved or more accurate result from the one or more machine learning models. In response, the computer system can modify the received request using data from the other request. For example, the computer system can adjust at least one of (i) a semantics of the third request, (ii) a number of words of the third request, (iii) data types of words in the third request, (iv) word types in the third request, and (v) order of the words in the third request. In response, the computer system can provide the modified third request to the one or more machine learning models, obtain an output from the one or more machine learning models for processing the modified third request, and providing the obtained output and a notification that the third request was modified to a third user device that submitted the third request.

In some implementations, the computer system can determine that a fourth request of the multiple request is similar to the one or more other stored requests within a threshold value. For example, the computer system may compare various criteria of the fourth request to various criteria of a set of the one or more other requests, the set of other requests were previously provided to the one or more machine learning models and subsequently caused the one or more machine learning models to perform at least one of a hallucination, breaking, or timing out. Based on the comparison, the computer system can determine whether the various criteria of the fourth request satisfy the various criteria of a set of the one or more other requests. In response to determining that the various criteria of the fourth request satisfy at least one criterion of the set of the one or more other requests, the computer system can predict that that the fourth request is likely to cause the one or more machine learning models to perform at least one of the hallucination, the breaking, or the timing out.

Based on the prediction that the one or more machine learning models is likely to hallucinate, break, or time out in response to processing the received fourth request, the computer system can modify, using data from a second set of other requests, the fourth request for querying the one or more machine learning model. The modification can include, for example, adjusting at least one of (i) a semantics of the fourth request, (ii) a number of words of the fourth request, (iii) data types of words in the fourth request, (iv) word types in the fourth request, and (v) order of the words in the fourth request, to name some examples.

In response to modifying the fourth request, the computer system can provide, to the one or more machine learning models over a network, the modified fourth request. The computer system can obtain the output from the machine learning models in response to processing the fourth request. Using the output, the computer system can identify that the output indicates the one or more machine learning models did not perform at least one of the hallucination, the breaking, or the timing out in response to processing the fourth request. The computer system can provide, to a fourth user device that submitted the fourth request, the other output from the one or more machine learning models and data indicating the modification to the fourth request.

In some implementations, the computer system can predict one or more subsequent queries a user is likely to submit based on (i) a received request, and (ii) the one or more other requests that previously queried the one or more machine learning models. If the computer system determines that a received request is similar to one or more other requests, then the computer system can predict other requests, such as in a series of previous requests sent to the one or more machine learning models, the user is likely to submit. In response, the computer system can transmit, over a network and to the client device of the user, the predicted requests as recommendations that the user is likely to subsequently provide. In this instance, the computer system may estimate queries the user is likely to submit prior to the user submitting these queries.

Various implementations of the systems and techniques described here can be realized in digital electronic circuitry, integrated circuitry, specially designed ASICs, computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs, also known as programs, software, software applications or code, include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device, e.g., magnetic discs, optical disks, memory, Programmable Logic Devices (PLDs) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The systems and techniques described here can be implemented in a computing system that includes a back-end component, e.g., as a data server, or that includes a middleware component such as an application server, or that includes a front-end component such as a client computer having a graphical user interface or a Web browser through which a user can interact with an implementation of the systems and techniques described here, or any combination of such back-end, middleware, or front-end components. The components of the system can be interconnected by any form or medium of digital data communication such as, a communication network. Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

Although a few implementations have been described in detail above, other modifications are possible. For example, while a client application is described as accessing the delegate(s), in other implementations the delegate(s) may be employed by other applications implemented by one or more processors, such as an application executing on one or more servers. In addition, the logic flows depicted in the figures do not require the particular order shown, or sequential order, to achieve desirable results. In addition, other actions may be provided, or actions may be eliminated, from the described flows, and other components may be added to, or removed from, the described systems. Accordingly, other implementations are within the scope of the following claims.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A computer-implemented method performed by one or more computers comprising:

receiving multiple requests related to clinical trial data for querying one or more machine learning models;

determining whether a first request of the multiple requests corresponds to one or more other requests that previously queried the one or more machine learning models;

in response to determining that the first request of the multiple requests corresponds to the one or more other requests:

retrieving a first natural language response previously produced by the one or more machine learning models associated with the first request; and providing, to a first user device that submitted the first request, the first retrieved natural language response;

determining whether a second request of the multiple requests corresponds to the one or more other requests that previously queried the one or more machine learning models; and in response to determining that the second request does not correspond to any of the one or more other requests:

providing, to the one or more machine learning models, the second request; and providing, to a second user device that submitted the second request, a second natural language response to the second request output from the one or more machine learning models.

2. The computer-implemented method of claim 1, wherein receiving the multiple requests related to the clinical trial data for querying the one or more machine learning models comprises receiving the multiple requests provided by a respective user through an interface of a respective user device, each request of the multiple requests comprising a natural language question for querying the one or more machine learning models.

3. The computer-implemented method of claim 1, wherein determining whether a given request of the multiple requests corresponds to one or more other requests that previously queried the one or more machine learning models comprises:

identifying characteristics of the given request, wherein identifying the characteristics of the given request comprises:

parsing words in the given request into separate words;

identifying a number of parsed words in the given request;

identifying a meaning of each parsed word in the given request; and identifying a contextual domain of the given request using the meaning of each parsed word and the number of parsed words in the given request.

4. The computer-implemented method of claim 3, wherein determining whether the given request of the multiple requests corresponds to the one or more other requests that previously queried the one or more machine learning models comprises:

for each other request of a plurality of other requests:

comparing the contextual domain of the given request with the contextual domain of the other request;

determining whether the comparison between the contextual domain of the given request and the contextual domain of the other request correspond to one another according to a threshold metric; and in response to determining the comparison satisfies the threshold metric, retrieving the other request and a natural language response that was produced by the machine learning models from processing the other request.

5. The computer-implemented method of claim 1, further comprising:

in response to determining that a given request of the multiple requests corresponds to the one or more of other requests:

modifying, using data from the one or more other requests identified as corresponding to the given request, the given request for querying the one or more machine learning models, the modifying comprises:

modifying, using the data from the one or more other requests identified as corresponding to the given request, the given request by adjusting at least one of (i) a semantics of the given request, (ii) a number of words of the given request, (iii) data types of words in the given request, (iv) word types in the given request, and (v) order of the words in the given request;

providing, to the one or more machine learning models, the modified given request; and providing, to a user device, another output from the one or more machine learning models that processed the given request.

6. The computer-implemented method of claim 1, further comprising:

in response to determining that a given request corresponds to the one or more other requests:

comparing criteria of the given request to criteria of a set of the one or more other requests, the set of the one or more other requests having previously caused the one or more machine learning models to hallucinate, break, or time out;

based on the comparison, determining whether the criteria of the given request satisfy the criteria of the set of the one or more other requests;

in response to determining that the criteria of the given request satisfy at least one criterion of the set of the one or more other requests, predicting that the given request is likely to cause the one or more machine learning models hallucinate, break, or time out; and in response to the prediction, modifying, using data from a second set of other requests, the given request to prevent the one or more machine learning models from hallucinating, breaking, or timing out in response to processing the given request.

7. The computer-implemented method of claim 6, further comprising:

providing, to the one or more machine learning models, the modified given request;

obtaining another output from the one or more machine learning models that processed the given request;

identifying that the another output indicates the one or more machine learning models did not hallucinate, break, or time out in response to processing the given request; and providing, to a user device the anther output from the one or more machine learning models and data indicating the modification to the given request.

8. The computer-implemented method of claim 1, wherein providing the second request comprises transmitting, over a network and to the one or more machine learning models, the second request and metadata associated with the second request selected from a database.

9. The computer-implemented method of claim 1, further comprising providing, to the one or more machine learning models, a request for one or more software instructions utilized by the one or more machine learning models in producing the second natural language response for processing the second request.

10. The computer-implemented method of claim 9, further comprising:

obtaining the second natural language response from the one or more machine learning models that processed the second request;

storing, in a database, an obtained output and one or more software instructions from the one or more machine learning models with the second request;

generating output from locally executing, using one or more processors, one or more software instructions using data from the database, the one or more software instructions utilized by the one or more machine learning models in producing the output for processing the second request; and comparing the (i) generated output from locally executing the one or more software instructions received from the one or more machine learning models and (ii) the obtained output from the one or more machine learning models.

11. The computer-implemented method of claim 10, in response to comparing the (i) generated output from locally executing the one or more software instructions received from the one or more machine learning models and (ii) the obtained output from the one or more machine learning models, the method comprises providing, to the second user device, data indicative of the obtained output that processed the second request in response to determining the generated output corresponds to the obtained output.

12. The computer-implemented method of claim 10, in response to comparing the (i) generated output from locally executing the one or more software instructions received from the machine learning models and (ii) the obtained output from the one or more machine learning models, the method comprises:

determining whether the generated output does not correspond to the obtained output from the one or more machine learning models; or determining whether the local execution of the one or more software instructions received from the one or more machine learning models is unable to be executed; and in response to determining that the generated output does not correspond to the obtained output or determining that the local execution of the one or more software instructions received from the one or more machine learning models is unable to be executed, providing, to the second user device, data indicating that the one or more machine learning models cannot process the second request.

13. The computer-implemented method of claim 4, further comprising:

monitoring communications between multiple user devices and the one or more machine learning models, wherein the monitoring comprises:

obtaining the plurality of other requests that previously queried the one or more machine learning models;

obtaining a plurality of natural language responses from the one or more machine learning models associated with the plurality of other requests;

in response, generating metadata for each other request of the plurality of other requests and for each natural language response of the plurality of natural language responses; and storing, in a database, the plurality of other requests, corresponding plurality of natural language responses, and corresponding metadata, wherein each other request, corresponding natural language response, and corresponding metadata is stored in an indexable fashion.

14. The computer-implemented method of claim 1, further comprising:

in response to determining that the first request corresponds to the one or more other requests, predicting one or more subsequent queries a user device is likely to submit based on (i) the first request and (ii) the one or more other requests that previously queried the one or more machine learning models; and transmitting, over a network, the one or more subsequent queries to the user device as recommendations, wherein the one or more subsequent queries are recommended to a user of the user device as queries the user is likely to subsequently provide.

15. A system comprising:

one or more computers and one or more storage devices storing instructions that are operable, when executed by the one or more computers, to cause the one or more computers to perform operations comprising:

receiving multiple requests related to clinical trial data for querying one or more machine learning models;

determining whether a first request of the multiple requests corresponds to one or more other requests that previously queried the one or more machine learning models;

in response to determining that the first request of the multiple requests corresponds to the one or more other requests:

retrieving a first natural language response previously produced by the one or more machine learning models associated with the first request; and providing, to a first user device that submitted the first request, the first retrieved natural language response;

determining whether a second request of the multiple requests corresponds to the one or more other requests that previously queried the one or more machine learning models; and in response to determining that the second request does not correspond to any of the one or more other requests:

providing, to the one or more machine learning models, the second request; and providing, to a second user device that submitted the second request, a second natural language response to the second request output from the one or more machine learning models.

16. The system of claim 15, wherein receiving the multiple requests related to the clinical trial data for querying the one or more machine learning models comprises receiving the multiple requests provided by a respective user through an interface of a respective user device, each request of the multiple requests comprising a natural language question for querying the one or more machine learning models.

17. The system of claim 15, wherein determining whether a given request of the multiple requests corresponds to the one or more other requests that previously queried the one or more machine learning models comprises:

identifying characteristics of the given request, wherein identifying the characteristics of the given request comprises:

parsing words in the given request into separate words;

identifying a number of parsed words in the given request;

identifying a meaning of each parsed word in the given request; and identifying a contextual domain of the given request using the meaning of each parsed word and the number of parsed words in the given request.

18. The system of claim 17, wherein determining whether the given request of the multiple requests corresponds to the one or more other requests that previously queried the one or more machine learning models comprises:

for each other request of a plurality of other requests:

comparing the contextual domain of the given request with a contextual domain of the other request;

determining whether the comparison between the contextual domain of the given request and the contextual domain of the other request correspond to one another according to a threshold metric; and in response to determining the comparison satisfies the threshold metric, retrieving the other request and a natural language response that was produced by the one or more machine learning models from processing the other request.

19. The system of claim 15, further comprising:

in response to determining that a given request of the multiple requests corresponds to the one or more other requests:

modifying, using data from the one or more other requests identified as corresponding to the given request, the given request for querying the one or more machine learning models, the modifying comprises:

modifying, using the data from the one or more other requests identified as corresponding to the given request, the given request by adjusting at least one of (i) a semantics of the given request, (ii) a number of words of the given request, (iii) data types of words in the given request, (iv) word types in the given request, and (v) order of the words in the given request;

providing, to the one or more machine learning models, the modified given request; and providing, to the user device, another output from the one or more machine learning models that processed the given request.

20. A non-transitory computer-readable medium storing software comprising instructions executable by one or more computers which, upon such execution, cause the one or more computers to perform operations comprising:

receiving multiple requests related to clinical trial data for querying one or more machine learning models;

determining whether a first request of the multiple requests corresponds to one or more other requests that previously queried the one or more machine learning models;

in response to determining that the first request of the multiple requests corresponds to the one or more other requests:

retrieving a first natural language response previously produced by the one or more machine learning models associated with the first request; and providing, to a first user device that submitted the first request, the first retrieved natural language response;

determining whether a second request of the multiple requests corresponds to the one or more other requests that previously queried the one or more machine learning models; and in response to determining that the second request does not correspond to any of the one or more other requests:

providing, to the one or more machine learning models, the second request; and providing, to a second user device that submitted the second request, a second natural language response to the second request output from the one or more machine learning models.

* * * * *